(12) United States Patent
Beekman

(10) Patent No.: US 7,145,153 B2
(45) Date of Patent: Dec. 5, 2006

(54) METHOD OF OBTAINING A TOMOGRAPHIC IMAGE

(75) Inventor: Frederik Johannes Beekman, Utrecht (NL)

(73) Assignee: Universitair Medisch Centrum Utrecht, Utrecht (NL)

( * ) Notice: Subject to any disclaimer, the term of this patent is extended or adjusted under 35 U.S.C. 154(b) by 170 days.

(21) Appl. No.: 10/777,454

(22) Filed: Feb. 12, 2004

(65) Prior Publication Data

US 2004/0232348 A1 Nov. 25, 2004

(30) Foreign Application Priority Data

May 11, 2001 (NL) .................................... 1018060
May 8, 2002 (WO) ..................... PCT/NL02/00303

(51) Int. Cl.
*G01T 1/00* (2006.01)
(52) U.S. Cl. ............. 250/393; 250/363.01; 250/363.02
(58) Field of Classification Search ................ 250/393, 250/363.01, 363.02, 363.04, 363.07, 363.1, 250/366, 367, 505.1
See application file for complete search history.

(56) References Cited

U.S. PATENT DOCUMENTS

| | | | |
|---|---|---|---|
| 3,654,469 A | | 4/1972 | Kantor |
| 4,095,107 A | * | 6/1978 | Genna et al. .......... 250/363.04 |
| 4,118,632 A | | 10/1978 | Luig |
| 4,228,515 A | * | 10/1980 | Genna et al. ............... 356/319 |
| 4,408,124 A | * | 10/1983 | Paras ....................... 250/252.1 |
| 4,507,733 A | * | 3/1985 | Blum ..................... 250/363.09 |
| H000012 H | * | 1/1986 | Bennett et al. ........ 250/363.09 |
| 4,584,478 A | * | 4/1986 | Genna et al. .......... 250/363.04 |
| 4,593,198 A | * | 6/1986 | Pang et al. ................. 250/366 |
| 4,748,328 A | * | 5/1988 | Chang et al. .......... 250/363.04 |
| 4,873,632 A | * | 10/1989 | Logan et al. .......... 250/363.02 |
| 4,959,547 A | * | 9/1990 | Carroll et al. ........... 250/336.1 |
| 5,021,667 A | | 6/1991 | Genna et al. |
| 5,023,895 A | * | 6/1991 | McCroskey et al. ............ 378/4 |
| 5,289,008 A | * | 2/1994 | Jaszczak et al. ....... 250/363.03 |
| 5,291,021 A | * | 3/1994 | Tanaka et al. ......... 250/363.03 |
| 5,448,611 A | * | 9/1995 | Kerjean ....................... 378/65 |
| 5,502,303 A | * | 3/1996 | Gonzalez-Lepera ...... 250/252.1 |
| 5,543,622 A | * | 8/1996 | Stearns ................... 250/363.03 |
| 5,751,000 A | * | 5/1998 | McCroskey et al. ... 250/363.03 |
| 6,040,580 A | * | 3/2000 | Watson et al. ......... 250/363.03 |
| 6,275,561 B1 | * | 8/2001 | Danielsson ................. 378/15 |
| 6,324,258 B1 | * | 11/2001 | Beekman .................... 378/145 |
| 6,353,227 B1 | * | 3/2002 | Boxen ...................... 250/363.1 |
| 6,380,540 B1 | * | 4/2002 | Maor et al. ............ 250/363.04 |

(Continued)

FOREIGN PATENT DOCUMENTS

EP 0 506 023 A 9/1992

(Continued)

*Primary Examiner*—David Porta
*Assistant Examiner*—Faye Boosalis
(74) *Attorney, Agent, or Firm*—Altera Law Group, LLC

(57) ABSTRACT

A method of obtaining a tomographic image of part of an animal or a part of an animal including a human being or a part of a human being by using radioactive radiation is disclosed. The animal is at least partly placed into a measuring cavity having an axial axis. The measuring cavity being at least partially surrounded by a cavity wall which is provided with a plurality of pinholes, and behind the pin holes (as viewed from the measuring cavity or lumen) detection means are placed. A radioactive radiation from a radioactive isotope administered to the animal is detected in a position-related manner by the detection means and data obtained with the detection means are used for the generation of the tomographic image.

89 Claims, 15 Drawing Sheets

U.S. PATENT DOCUMENTS

| | | | |
|---|---|---|---|
| 6,411,670 B1 * | 6/2002 | Besson | 378/4 |
| 6,420,711 B1 * | 7/2002 | Tumer | 250/370.09 |
| 6,429,434 B1 * | 8/2002 | Watson et al. | 250/363.04 |
| 6,803,580 B1 * | 10/2004 | Wainer | 250/363.04 |
| 6,915,004 B1 * | 7/2005 | Newport et al. | 382/131 |
| 6,931,096 B1 * | 8/2005 | Carlsson et al. | 378/65 |
| 6,963,065 B1 * | 11/2005 | Conti et al. | 250/252.1 |
| 7,012,257 B1 * | 3/2006 | Juni | 250/363.04 |
| 2004/0097800 A1 * | 5/2004 | Crosetto | 600/407 |
| 2006/0065848 A1 * | 3/2006 | Ueno et al. | 250/370.15 |

FOREIGN PATENT DOCUMENTS

| | | |
|---|---|---|
| WO | 0038197 | 6/2000 |

\* cited by examiner

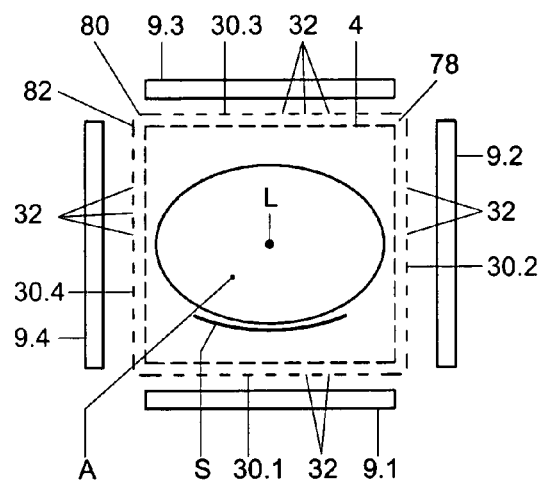
Fig. 17e
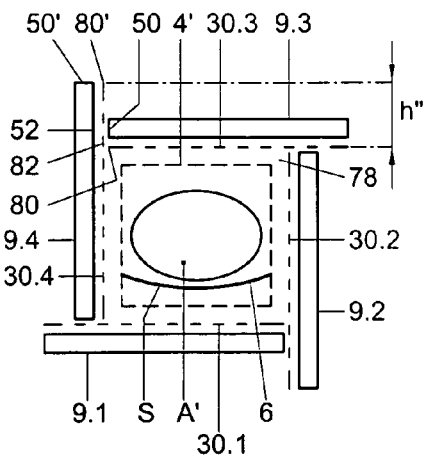
Fig. 17f
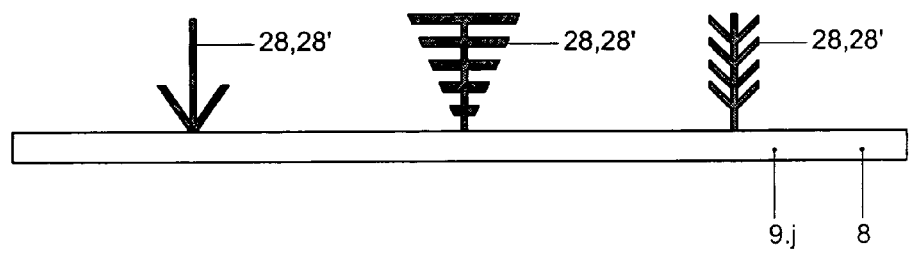
Fig. 18

METHOD OF OBTAINING A TOMOGRAPHIC IMAGE

BACKGROUND OF THE INVENTION

The invention relates to a method of obtaining a tomographic image of part of an animal or a part of an animal including a human being or a part of a human being by using radioactive radiation, wherein the animal is at least partly placed into a measuring cavity, the measuring cavity being at least partially surrounded by a cavity wall which is provided with a plurality of pinholes, and wherein behind the pin holes (as viewed from the measuring cavity) detection means are placed, radioactive radiation from a radioactive isotope administered to the animal is detected in a position-related manner by the detection means and data obtained with the detection means are used for the generation of the tomographic image.

The invention also relates to an apparatus for obtaining a tomographic image of a human being or part of a human being or an animal or a part thereof using radioactive radiation, which apparatus comprises a measuring cavity having an axial axis, a cavity wall which at least partly, surrounds the measuring cavity which cavity wall is provided with a plurality of pinholes, the apparatus further comprising detection means which viewed from the cavity, are provided behind the pin holes, wherein the detection means are arranged for receiving, in a position-related manner, the radioactive radiation emitted within the measuring cavity and wherein the detection means can be read electronically or optically.

Such a method and apparatus are known in the art for making tomographic images of animals, including humans, revealing a biological activity (in the case where a compound comprising an isotope to be measured is bound or metabolised) or giving an indication of which locations an isotope can reach. The detection means is a position-sensitive detection means which detects the radiation which falls on the detection means wherein the detection means also registers the position on the detection means which receives the radiation. In other words the radiation is detected in a position related manner. The detection means may also detect the strength (energy of the photons or other radiated particles) of the radiation which is detected on a certain position.

There is need of a method providing a more sensitive way of measuring. This would either allow a reduction of the load of radioactive material used for measuring the animal, or it would allow a biological measurement as described above to be carried out with more precision. There is also a need for measuring at a higher resolution. These requirements of greater sensitivity and higher resolution are in part conflicting.

BRIEF SUMMARY OF THE INVENTION

It is the object of the present application to provide a method and apparatus which provide a solution for at least one of such needs. To this end, according to one aspect of the invention the method is characterised in that—the pinholes are at least substantially arranged in a plurality of flat planes which planes are at least substantially parallel and separated in the axial direction relative to each other wherein the distance between neighbouring planes is smaller than the distance between neighbouring pinholes within such a plane; or the pinholes are at least substantially arranged along a helix wherein the pitch of the helix is generally smaller than the distance between neighbouring pinholes laying on the helix.

Preferably the planes are each at least substantially directed perpendicular to the axial direction. According to a special embodiment, the apparatus is characterised in that the distance between neighbouring planes is at least 1.3, more specifically at least 2, preferably at least 5 and more preferably a least 10 times smaller than the distance between neighbouring pinholes within any of such planes; or the pitch of the helix is generally at least 1.3, more specifically at least 2, preferably at least 5 and more preferably at least 10 times smaller than the distance between neighbouring pinholes laying along the helix. However also embodiments wherein the distance between neighbouring planes is only slightly smaller (for example 1.03 or 1.05 times smaller) than the distance between neighbouring pinholes within any of such planes fall within the scope of the present invention. Also embodiments wherein the pitch of the helix is only slightly (for example 1.03 or 1.05 times) smaller than the distance between neighbouring pinholes laying along the helix fall within the scope of the invention.

Despite deviating from the standard manner of positioning pinholes, an adequate width of the field of view (transversally) is maintained, and the animal or part of the animal may be viewed from numerous angles. Because the radiation detected by a detection means on average enters the pinholes at a less oblique angle, (i) more radiation quanta per volume element of the measuring cavity are allowed to pass through so that the noise in the image will be reduced, and (ii) better image reconstruction becomes possible because fewer parts of the object to be measured, e.g. an animal, need to be reconstructed from measurements that are less suitable (i.e. from oblique angles). The article by Rogulski et al (IEEE Trans. Nucl. Sci. Pp 1123–1129—(1993)) describes a method of performing image reconstruction for a multiple pinhole system. The invention is based on the insight that in case the distance between said planes would hypothetically be zero an exact reconstruction of a cross section of the object would be possible. This is however practically not possible. The invention provides a solution to this problem by not merely selecting the distance between neighbouring planes as small as possible but by selecting the distance between neighbouring planes according to a certain condition relative to the distance between neighbouring pinholes within said planes. In practice, it shows that if this condition is met a surprisingly improved reconstruction of a cross section of the object is possible.

According to a special embodiment, the cavity wall comprises a number of at least substantially flat wall segments having the pinholes. Because of the use of such wall segments the cavity wall can be obtained in a relatively easy manner.

According to an advantageous embodiment, the apparatus is further characterized in that an edge directed in the axial direction of at least one of the wall segments is adjacent to a selectable portion of a neighbouring wall segment said portion being directed in the axial direction and facing the measuring cavity so that the diameter of the measuring cavity can be varied by selecting the distance between said portion of said neighbouring wall segment and an edge directed in the axial direction of said neighbouring wall segment and/or that the detection means comprises a plurality of substantially flat detectors wherein an edge directed in the axial direction of at least one of the detectors is adjacent to a selectable portion of a neighbouring detector said portion being directed in the axial direction and facing the measuring cavity so that the diameter of a cavity formed by the detectors can be varied by selecting the distance between said portion of said neighbouring wall detector and an edge directed in the axial direction of said neighbouring detector. Hence, the size of the measured cavity may be varied by adjusting the portions of the wall segments relative to each other.

If the size of the cavity is adjusted this means that, in use, the distance between at least some of the pinholes and the animal or human being is adjusted as well. This implies that the magnification of the image is adjusted accordingly. Also the size of the cavity can be adapted to the size of (the parts of) the animal or human being to be observed.

According to another aspect of the invention, the apparatus is characterised in that the apparatus is further provided with radiation blocking means which partly block radiation which travels from the measuring cavity through at least one of the pinholes to the detection means such that the radiation which is detected by the detection means lays in a limited solid angle relative to the at least one pinhole, which angle is smaller than the solid angle which would have been obtained without the radiation blocking means. The limited solid angle may provide a higher image resolution and can facilitate configurations that allow for obtaining a higher sensitivity because the number of pinholes may be increased wherein it can be guaranteed that radiation coming from different pinholes will not be detected by one and the same element (or detection array) of the detection means. This can even be obtained if the distance between the pinholes on the one hand and the detection means on the other hand is enlarged for obtaining a greater magnification because by means of the radiation blocking means it can be guaranteed that radiation coming from different pinholes will not be detected by one and the same element (or detection array) of the detection means.

According to a special embodiment, the radiation blocking means comprises baffles. The baffles may be located inside the measuring cavity. In case the baffles are located inside the measuring cavity, the baffles may be located adjacent the cavity wall. The baffles may, however, also be located outside the measuring cavity. In case that the baffles are located outside the measuring cavity, the baffles may be adjacent to the cavity wall. Alternatively, the baffles may be adjacent to the detection means. According to a preferred embodiment, the baffles each lay substantially in a plane through said axial axis.

According to an alternative embodiment, the radiation blocking means comprise a blocking wall extending between the cavity wall and the detection means wherein said blocking wall comprises a plurality of openings for providing a passage for the radiation from the pinholes to the detection means laying within said limited solid angle. The openings generally have a surface which is larger than the surface of the pinholes on the one hand and is small enough to provide said limited solid angle on the other hand.

According to a special embodiment, each opening of the blocking wall corresponds with one of the pinholes such that the radiation, which passes through one of the openings, comes from one of the pinholes. It holds that radiation, which comes from one of the pinholes, will only reach the detection means by passing through one of the openings.

It is noted that the radiation blocking means may advantageously be used in combination with the above discussed possibility for varying the size of the cavity and/or varying the distance between the cavity wall and the detection means.

The invention also relates to a method of obtaining a tomographic image of a human being or part of a human being or an animal or a part thereof using radioactive radiation, which apparatus comprises a measuring cavity provided with a plurality of pinholes, the measuring cavity being arranged to, at least partly, surround the animal where, viewed from the lumen, detection means D are provided behind the pin holes, where the detection means D are suitable for, in a position-dependent manner, detecting radioactive radiation and that the detection means D can be read electronically or optically, characterised in that the wall of the measuring cavity possesses an array of pinholes, wherein the axial component of the distance between two in axial direction neighbouring pinholes is smaller than the transversal component of the distance between two neighbouring pinholes located in transversal direction with respect to the axial direction, in that a pinhole $P_i$ has a maximum angle of incidence $a_i$ with respect to the normal and a detection means $D_i$ located behind that pinhole, and in that means are provided to limit the chance that via pinhole $P_i$ radiation reaches any detection means D other than detection means $D_i$.

It is possible to reduce the chance of radiation via pinhole $P_i$ reaching a detection means D other than the detection means $D_i$, by adjusting the distance between a detection means $D_i$, which is located behind a pinhole $P_i$ and the pinhole $P_i$. This can be done, in particular, by using means for reducing the distance until the desired degree of reduction is reached. The detection means $D_i$ which, viewed from the lumen, is located behind a pinhole $P_i$ may be comprised of one single position-independent detector or, and this is preferred, of a position-dependent detector. A position-independent detector is a detector which detects the radiation which falls on the detector wherein the detector does not register the position on the detector which receives the radiation. A position-dependent detector is a position-sensitive detector which detects the radiation which falls on the detector wherein the detector also registers the position on the detector which receives the radiation. In other words, the radiation is detected in a position related manner. A combination of a plurality of position-independent detectors may form a position-dependent detector. The position-dependent detector may comprise a plate of photoluminescent material such as NaI, behind which photo multipliers are placed. The position-dependent detector may also be comprised of one or several (parts of) detector arrays of position-independent detection elements. More specifically, the detector arrays may be radiation-sensitive semiconductor arrays, such as detector arrays based on CdZnTe or CdTe. The detection means D may also be part of a larger detector, in which case that detector has to be a position-dependent detector. In order to reduce the chance of radiation via pinhole $P_i$ falling on detection means D other than detection means $D_i$, it is possible to direct the pinhole by placing it at an angle to the wall of the measuring cavity. Alternatively, the wall of the measuring cavity may be curved so that the pinhole is directed more towards the centre of the cavity or lumen. Furthermore the diameter of the pinhole in the transverse (circumferential) direction of the cavity may first decrease and than increase in a direction from the outside of the cavity to the inside of the cavity. An example of such a pinhole is a knife-edge pinhole. It is observed that $P_i$ in the present application indicates any arbitrary pinhole P, while the index i is used to indicate the relationship with a particular corresponding detection means $D_i$, with i again being the index.

The invention also relates to an apparatus for obtaining a tomographic image of an animal or a part thereof using radioactive radiation, which apparatus comprises a measuring cavity provided with a plurality of pinholes, the measuring cavity being arranged to, at least partly, surround the animal where, viewed from the lumen, detection means D are provided behind the pin holes, where the detection means D are suitable for in a position-dependent manner detecting radioactive radiation and that the detection means D can be read electronically or optically, characterised in that the wall of the measuring cavity possesses an array of pinholes, wherein an arbitrary first pinhole $P_1$ in a substantially axial direction in relation thereto has a nearest neighbouring pinhole $P_2$, and in a substantially transversal direction has a nearest neighbouring third pinhole $P_3$, the axial component of the distance between first and second pinholes $P_1$ and $P_2$, respectively, being smaller than the transversal component of the distance between the first and third pinholes $P_1$ and $P_3$, respectively, and in that means are provided to limit the chance that via pinhole Pi radiation reaches any detection means D other than detection means Di.

In this way an apparatus is provided with which the above-mentioned advantages can be achieved. When speaking of "smaller", the ratio between the transversal component of the (absolute) distance between two circumferentially neighbouring pin holes $P_1$ and $P_3$ and the axial component of the distance of two axially neighbouring pinholes $P_1$ and $P_2$, may for example be at least 1.3, preferably at least 2 and more preferably at least 5, and most preferably at least 10. However the ratio may also be slightly greater than 1 such as for example 1.03 or 1.05.

The means for reducing the chance of radiation via pinhole Pi reaching a detection means D other than the detection means Di is, for example, a device for adjusting the distance between a detection means Di located behind a pinhole Pi and the pinhole Pi. By this means the distance can be reduced until the desired degree of reduction has been reached. According to a preferred embodiment that may be used instead of, or in addition to the one mentioned above, the means comprise baffles.

Suitable positioning of the baffles, i.e. in the path along which radiation may unintentionally reach a detection means Di, may be realised very effectively and simply. To this end, the baffles are preferably directed at the (lumen of the) measuring cavity and more preferably the baffles are mounted on, around, or up against the surface of the detection means D. The baffles may be provided with projecting elements having a direction component parallel to the surface of the detection means.

According to a favourable embodiment it is preferred for the pinholes to be distributed over the wall of the measuring cavity such that for two peripherally neighbouring pinholes one axially neighbouring pinhole is situated halfway ±20% (that is 50±20% ) between the two peripheral neighbouring pinholes. Two peripherally neighbouring pinholes means that these pinholes are separated in the transversal direction.

In this way it is achieved that the object to be measured can be observed under several angles without rotation or translation of the measuring cavity in relation to the animal or that it can be viewed under numerous angles with only a limited number of rotations or translations and over a short distance. This makes the reconstruction of the tomographic image simpler/more reliable. Also, a relatively simple device can be employed. In addition, it increases the possibilities of recording a successive series of images and thus of monitoring changes in time.

To improve the imaging resolution, and/or by means of a simple translation to facilitate observation of the animal to be examined, which of course includes humans, from an increased number of angles, it is in addition or alternatively also possible for at least 3 transversally spaced from one another and axially nearest neighbouring pinholes Pi, to be axially staggered in relation to one another. That is to say, the pinholes are situated on a line that runs at an angle to the peripheral direction. This angle may be 20° or less, for example, 10° or less. To put it differently, the result is that the pinholes in the wall of the measuring cavity may have a spiral-like configuration. This is also referred to as a helix-like configuration meaning a configuration extending over three dimensions.

Although it is feasible to use a scintillating crystal behind which light detectors are provided as known in the art, it is preferable to use as detection means Di placed behind a pinhole Pi, a detector array, in particular a semiconductor detector array, such as a detector array based on CdZnTe or CdTe. Pixel, strip and crossed-strip detectors are also considered.

According to a favourable embodiment of the apparatus according to the invention that is simple to construct, the measuring cavity has a polygonal cross section and the wall is divided into wall segments having pinholes. Also, according to a special embodiment as indicated in claim 32 a polygonal construction may facilitate varying the distance between the detection means and the pinholes.

In order to increase the sensitivity and to help prevent radiation unintentionally reaching the detection means, pinholes that are located nearer the ribs of the polygonal measuring cavity are at an angle to the normal of the wall segment in the direction of the centre line of the polygonal measuring cavity. The number of viewing angles is also increased, resulting in the above-mentioned advantage. The angle between the pinholes and the normal is determined by the shape of the pinhole in the surface of the wall, and the angle is the mean angle of radiation. That is to say, the pinhole is able to let radiation through from several directions from the lumen. The angle referred to above is the mean of the angles of those directions.

For the same reasons, the pinholes near one of the ribs of the polygonal measuring cavity are preferably spaced further apart than pinholes nearer to the middle between two adjacent ribs; and pinholes situated nearer the axial ends of the measuring cavity may form an angle with the normal of the wall segment in the direction of the absolute centre of the measuring cavity.

In order to promote that radiation falls perpendicularly on a detection means Di, the detection means Di is preferably constructed of segments whose normal points from the centre of each segment to the pinhole Pi, or the detection means Di is curved, such that the normal at any arbitrary point of the detection means Di is oriented towards a pinhole Pi. In order to approximate the ideal spherical or cylindrical form, it is often simple to position at least two detection means Di based on semiconductors at an angle not in a plane in relation to one another. According to a preferred embodiment therefore a detection means Di situated behind a pinhole Pi comprises at least two detection means segments placed at an angle in relation to one another and out of plane, such that radiation from pinhole Pi reaching a detection means segment will, on average, have a more perpendicular line of incidence than if in case the segments were placed in a plane.

If the detection means Di include a photo-luminescent material or other detection material, the method can be carried out in a similar manner. In addition, or instead of this, the photo-luminescent material may have a concave shape as seen from the lumen of the cavity. In the latter case, the thickness of the photo-luminescent material is preferably kept constant by also curving the rear side in a corresponding manner. This may optionally also be cylindrical instead of spherical. In accordance with an alternative embodiment therefore, the detection means Di placed behind a pinhole Pi has a curved surface, such that the radiation from pinhole Pi will on average have a more perpendicular line of incidence onto each part of the detection means Di. In other words, on average the deviation of the line of incidence from the perpendicular line is smaller.

BRIEF DESCRIPTION OF THE SEVERAL VIEWS OF THE DRAWINGS

The invention will now be elucidated with reference to the following exemplary embodiments and the drawing, in which

FIG. 1b shows a view of a cavity wall of the apparatus according to FIG. 1a in a direction of the arrow P in FIG. 1a;

FIG. 2b shows a view of a cavity wall of the apparatus according to FIG. 2a in a direction of the arrow P in FIG. 2a;

FIG. 3b shows a view of a cavity wall of the apparatus according to FIG. 3a in a direction of the arrow P in FIG. 3a;

FIGS. 17e and 17f a cross section of a thirteenth embodiment of an apparatus according to the invention in a direction perpendicular to an axial axis of the apparatus; and FIG. 18 shows several embodiments of baffles.

DETAILED DESCRIPTION OF THE INVENTION

Figure 1A:
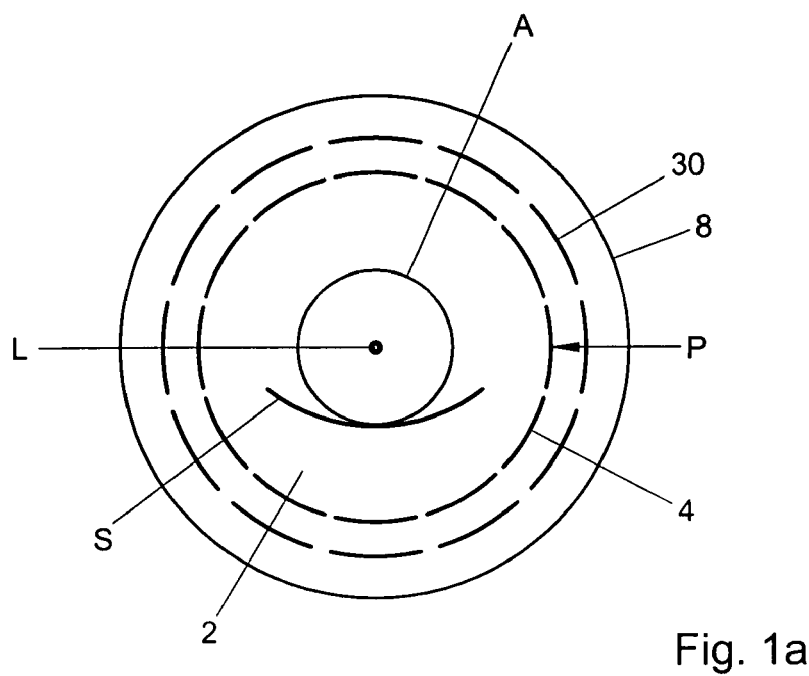
FIG. 1a shows a cross section perpendicular to an axial axis of a first embodiment of an apparatus according to the invention.

FIG. 1 shows an apparatus 1 for obtaining a tomographic image of a human being A, a part A of a human being, an animal A or part of an animal A, laying in this example on a supporting element S and using radioactive radiation. The apparatus 1 comprises a measuring cavity 2 having an axial axis L, and a cavity wall 4 which, at least partly, surrounds the measuring cavity 2. In this example the cavity wall 4 has the shape of a cylinder. The cavity wall 4 is provided with a plurality of pinholes 6.

The apparatus 1 is further provided with detection means 8 which, viewed from (the lumen of) the cavity, are provided behind the pinholes 6. In other words the cavity wall 4 comprising the pinholes is positioned between the detection means 8 and the cavity 2. The detection means 8 are arranged for receiving, in a position-related manner, radioactive radiation originating in the measuring cavity 2. This means that the detection means detects the radiation which falls on the detector wherein the detection means also registers the position on the detection means which receives the radiation. In other words the radiation is detected in a position related manner. The detection means may also register the strength of the radiation (for example energy of the photons or other radiated particles) which is detected on a certain position. The detection means are of a well-known type which can be read electronically or optically.

In this example the detection means 8 also have the shape of a cylinder. This is however not necessary. The detection means may also have a cross section perpendicular to the axis L, having a polygonal shape as will be discussed later.

Figure 1B:
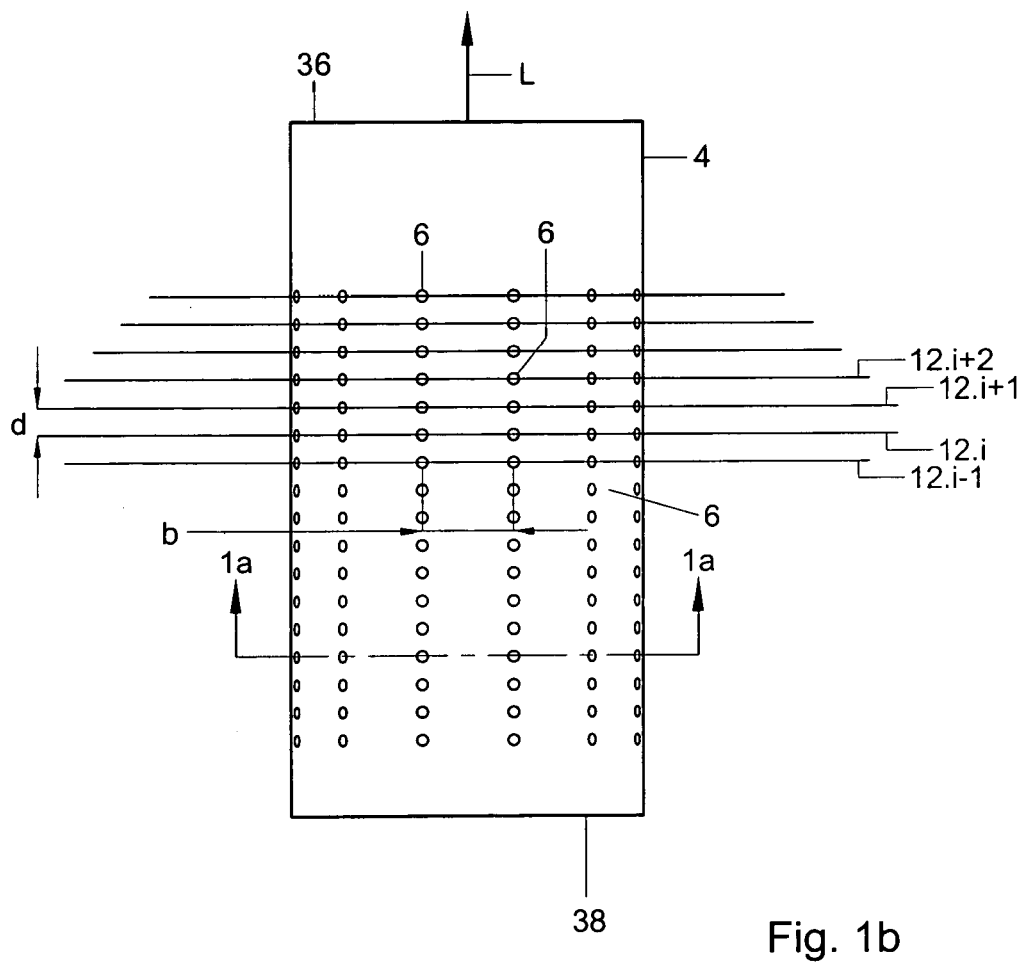

As can be seen best in FIG. 1b, the pinholes 6 are arranged in a plurality of flat planes 12.i (i=1,2,3, . . . n) which planes are substantially parallel to each other and separated in the direction of the axial axis L (also referred to as the axial direction) relative to each other. The distance d between the neighbouring planes 12.i and 12.i+1 is smaller than the distance b between neighbouring pinholes within such a plane 12.i or 12.i+1. Please note that in this application the distance between two neighbouring pinholes is defined as the distance between said pinholes along a straight line through said neighbouring pinholes. As a surprising effect according to the invention, if such a condition is met, the reconstruction of the image of in this example the animal A can be carried out more accurate then in case the distance b between neighbouring planes would be approximately the same as the distance between pinholes within neighbouring planes. This is based on the insight that in case the distance d would hypothetically be zero an exact reconstruction of a cross section of the object would be possible. This is however practically not possible. The invention provides a solution to this problem by not merely selecting the distance between neighbouring planes as small as possible but by selecting the distance between neighbouring planes relative to the distance between neighbouring pinholes within said planes according to a certain condition. In practice it shows that if this condition is met a surprisingly improved reconstruction of a cross section of the object is possible. In this example the planes are at least substantially directed perpendicular to the axial axis L. The direction of the planes relative to the axial axis may however also slightly vary in this respect.

Figure 2A:
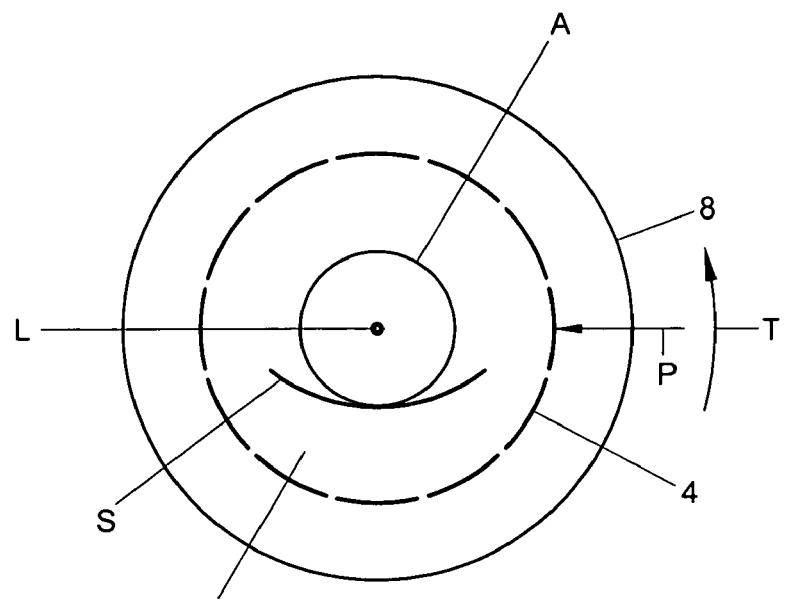
FIG. 2a shows a cross section perpendicular to an axial axis of a second embodiment of an apparatus according to the invention.
Figure 2B:
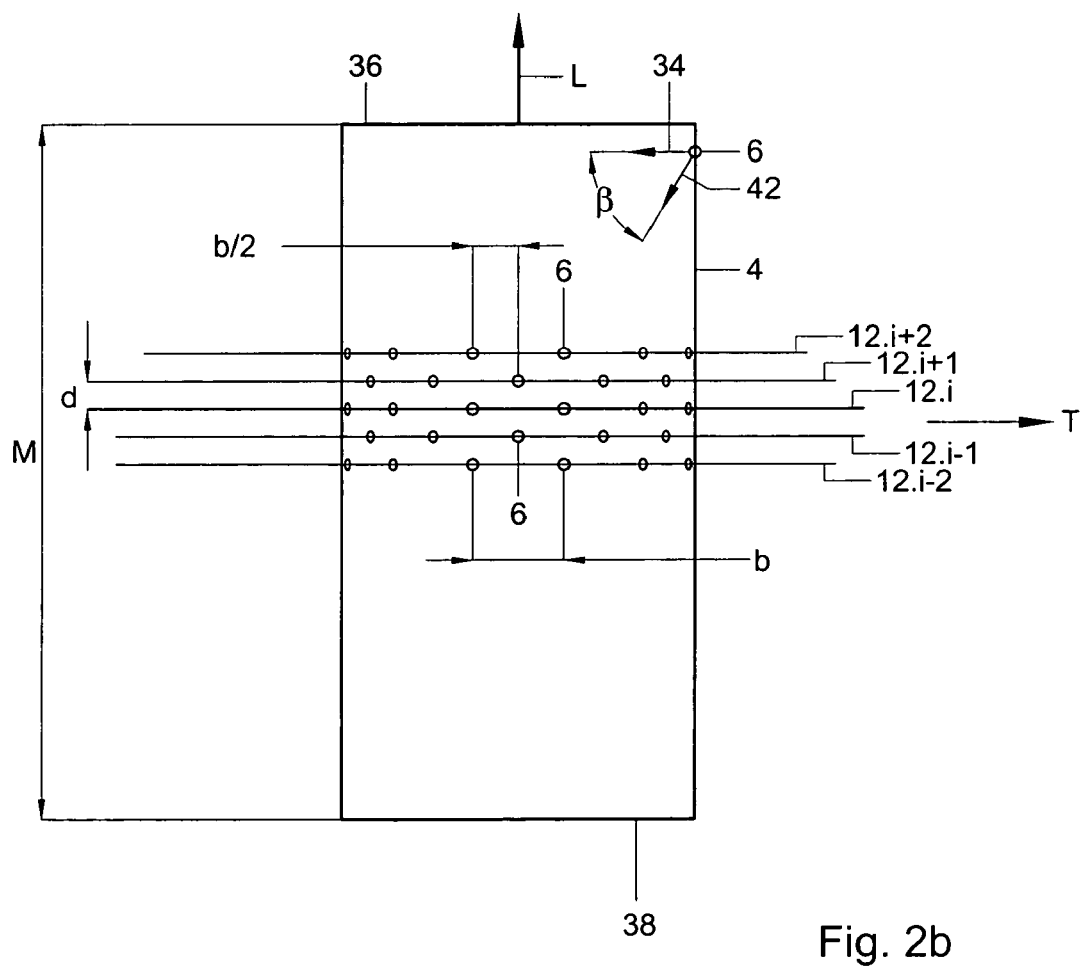

In FIGS. 2a and 2b an alternative embodiment of an apparatus 1 according to the invention is shown. In FIGS. 2a and 2b and FIGS. 1a and 1b parts corresponding with each other have the same reference numbers. As can be seen best from FIG. 2b the pinholes laying in the planes 12.i, wherein i is an even number, are staggered relative to the pinholes laying in the planes 12.i wherein i is an odd number. The staggering of the pinholes is in a transversal or tangential direction T. In this example the pinholes laying in the planes 12.i, wherein i is an even number, are staggered relative to the pinholes laying in the planes 12.i wherein i is an odd number over a distance which is equal to half the distance between neighbouring pinholes in a plane. Hence, the pinholes are staggered over a distance ½ b relative to each other. With a configuration as shown in FIG. 2 the same advantages can be obtained as discussed in relation with the apparatus according to FIG. 1. In this example, the pinholes laying in the planes 12.i, wherein i is an odd number or i is an even number, are not staggered relatively to each other. It is however possible that the pinholes laying in planes i+1 are staggered in the direction T over a distance ⅓ b relative to the pinholes laying in plane 12.i. The same applies to the pinholes laying in plane 12.i+2 relative to pinholes laying in planes 12.i+1. This implies that pinholes laying in planes 12.i+3 are not staggered to pinholes laying in plane 12.i. Such variations all fall within the scope of the invention. Hence, staggering between pinholes in neighbouring planes is also possible over other distances then ½ b or ⅓ b. The distances provided should be considered only as a possible example.

In FIG. 1 or 2 the distance between neighbouring planes may for example be at least 1.03, at least 1.05, at least 1.3, more specifically at least 2, preferably at least 5 or more preferably at least 10 times smaller than the distance between neighbouring pinholes within any of such planes. Preferably, on the other hand the distance between neighbouring planes may at the same time not be smaller than 0.03 and preferably 0.05 times the distance between neighbouring pinholes within any of such planes. Smaller distances between neighbouring planes are difficult to realize and provide only limited additional advantage. The distance between neighbouring planes may therefore for example be 0.03–0.98 and more preferably 0.05–0.77 times the distance between neighbouring pinholes within any of such planes.

FIG. 3 shows a third embodiment of an apparatus according to the invention. Parts of FIG. 1 and FIG. 3 which correspond with each other have been assigned the same reference number.

Figure 3A:
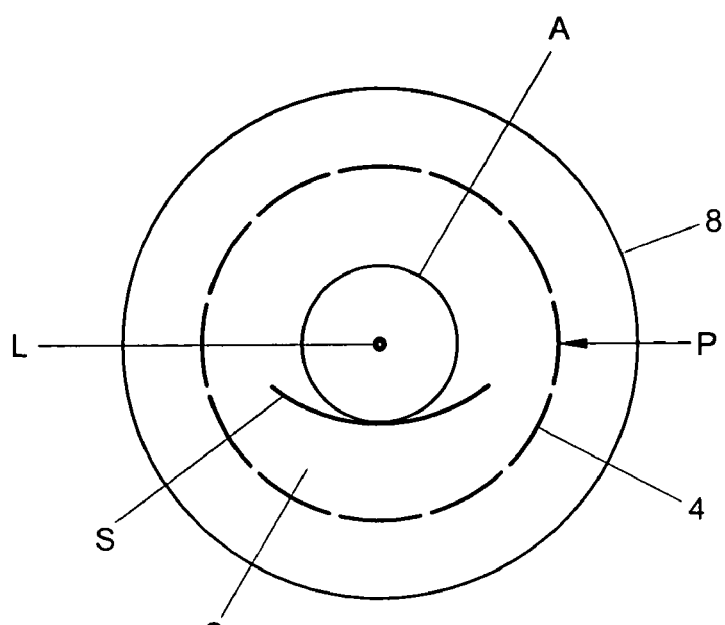
FIG. 3a shows a cross section perpendicular to an axial axis of a third embodiment of an apparatus according to the invention.
Figure 3B:
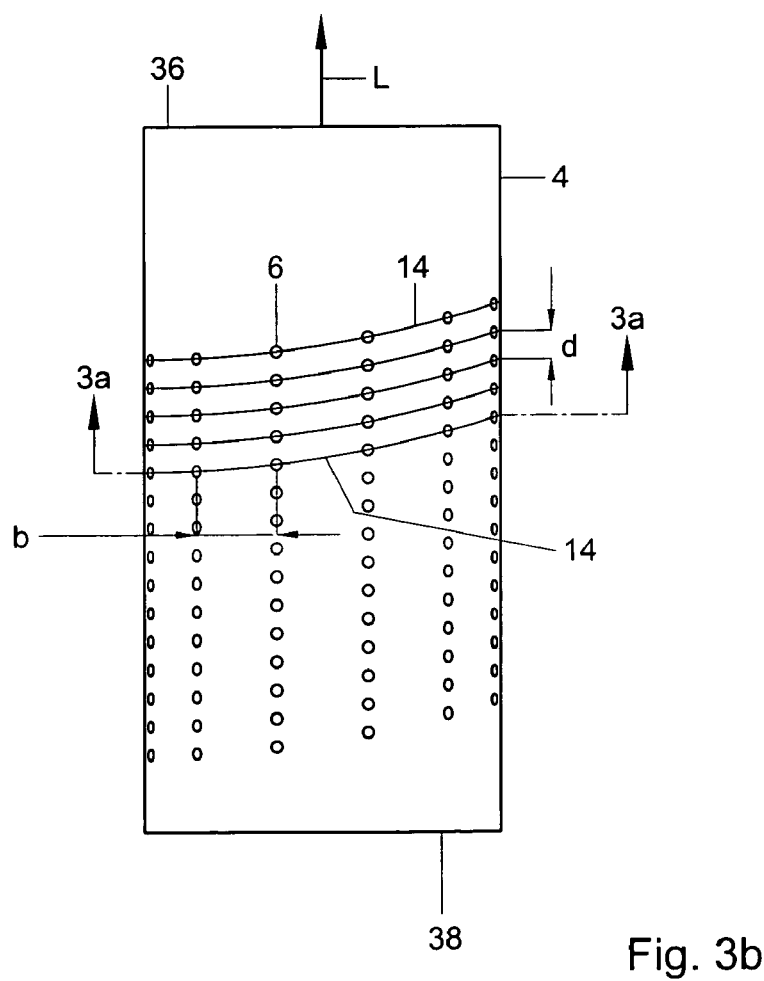

In the apparatus of FIGS. 3a and 3b, the pinholes 6 are arranged along a "virtual" helix which lays in the cavity wall 4. The pitch d of the helix is smaller than the distance between neighbouring pinholes b laying on the helix 14. The apparatus according to FIG. 3b has the same advantages as discussed in relation with the apparatus according to FIG. 1.

Figure 4:
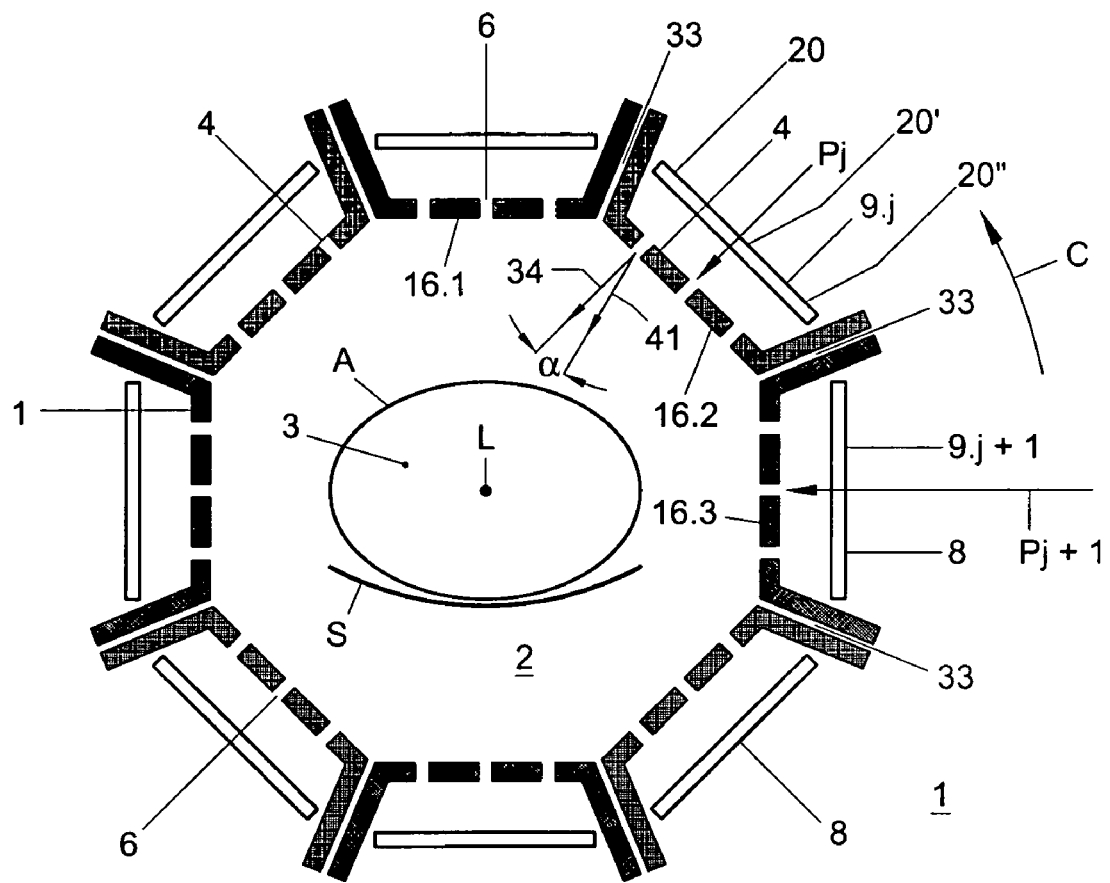
FIG. 4 shows a cross section perpendicular to an axial axis of a fourth embodiment of an apparatus according to the invention.

The pitch of the helix may be at least 1.03, at least 1.05, at least 1.3, more specifically at least 2, preferably at least 5 and more preferably at least 10 times smaller than the distance between neighbouring pinholes laying on the helix. Preferably, on the other hand the pitch of the helix may at the same time not be smaller than 0.03 and preferably 0.05 times the distance between neighbouring pinholes laying on the helix. A smaller pitch is difficult to realize and provides only limited additional advantage. The pitch of the helix may therefore for example be 0.03–0.98 and more preferably 0.05–0.77 times the distance between neighbouring pinholes laying on the helix. FIG. 4 shows a fourth possible embodiment according to the invention. As in the case with the embodiments shown in FIGS. 1–3, the cavity wall 4 is of a rotationally symmetrical design around the axial axis L of the measuring cavity 2. However, in this example the cavity wall 4 has a polygonal cross section in a direction perpendicular to the axial axis L. The cavity wall 4 is divided into eight at least substantially flat wall segments 16. Hence, the polygonal cross section comprises eight angles. Also the cavity wall 4 comprises eight wall segments. Each of the wall segments is provided with pinholes 6. These pinholes 6 may be arranged in a well-known pattern relative to each other. The detection means 8 of the apparatus according to FIG. 4 is provided with a plurality of substantially flat position sensitive detectors 9.j (j=1,2,3 . . . 8) wherein, in this example, a detector 9.j runs at least substantially parallel to a corresponding wall segment 16.j. A position sensitive detector may generate an output signal which amongst others depends on the position of the detector which receives said radiation. The output signal will also depend on the strength (amplitude or energy) of the radiation which is detected on a certain position.

As can be seen in the illustrated embodiment, an animal A or part of the animal (resting on a supporting element S) is completely surrounded by the cavity wall 4. Although this is favorable, it is not pre-requisited. The animal A or part thereof may also be surrounded over, for example, 225° in the transversal (also referred to as circumferential) direction C. A polygonal transversal cross section has the advantage that the circular form can be mimicked to a large extent, while the manufacture of the construction elements (wall segments 16.j and/or position-sensitive detectors 9.j) is simple. A polygon may have at least three, preferably at least four and suitably six or more wall segments 16.j.

Figure 5:
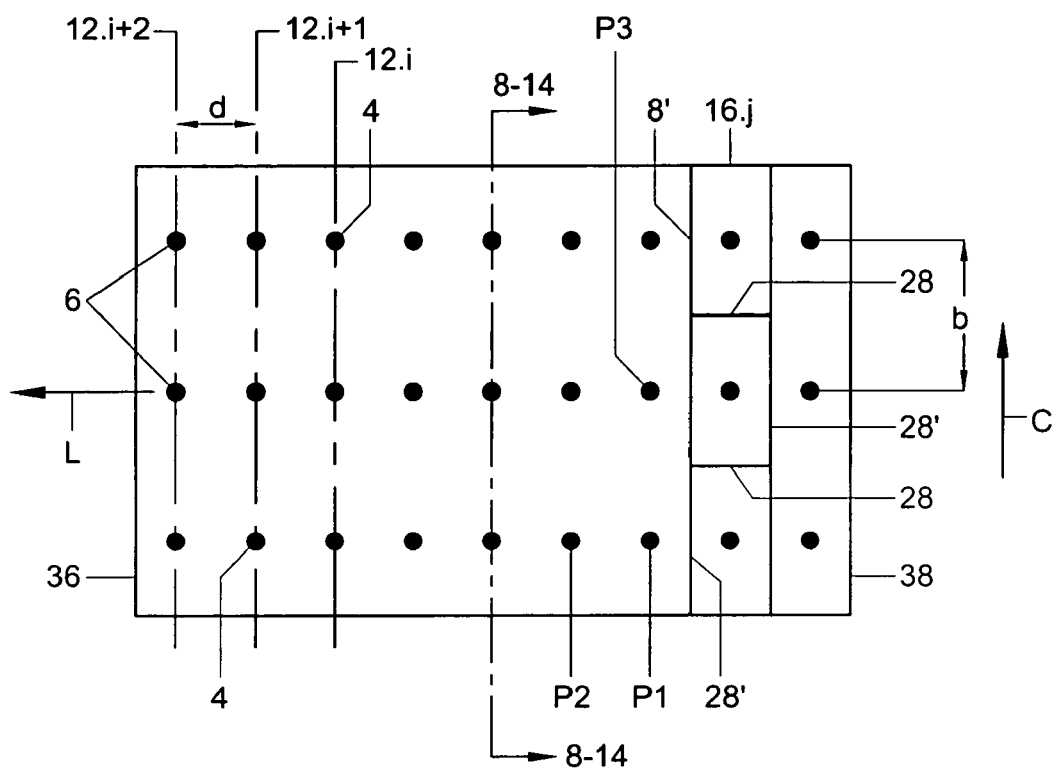
FIG. 5 shows a view of a first embodiment of a wall segment of the apparatus according to FIG. 4 in a direction as shown by the arrow Pj in FIG. 4.

The wall cavity, which is formed by the wall segments 16, is provided with the pinholes 6. The pinholes 6 may be arranged in a generally well-known pattern. The pinholes may however also be arranged as discussed in relation with FIGS. 1–3. An example of such an arrangement is shown in FIG. 5. FIG. 5 shows a possible arrangement of the pinholes in one of the wall segments 16.j. The pinholes of the wall segment 16.j and thereby the pinholes of the cavity wall 4 again lay in the substantially flat planes 12 which planes are parallel to each other and separated by a distance d. In this example the planes are each at least substantially perpendicular to the axial axis L. The normal of the planes may however also include a relatively small angle with said axial axis L. Furthermore, the neighbouring pinholes 6 laying within such a plane 12 are separated by a distance d wherein the distance d is smaller then the distance b.

Figure 6:
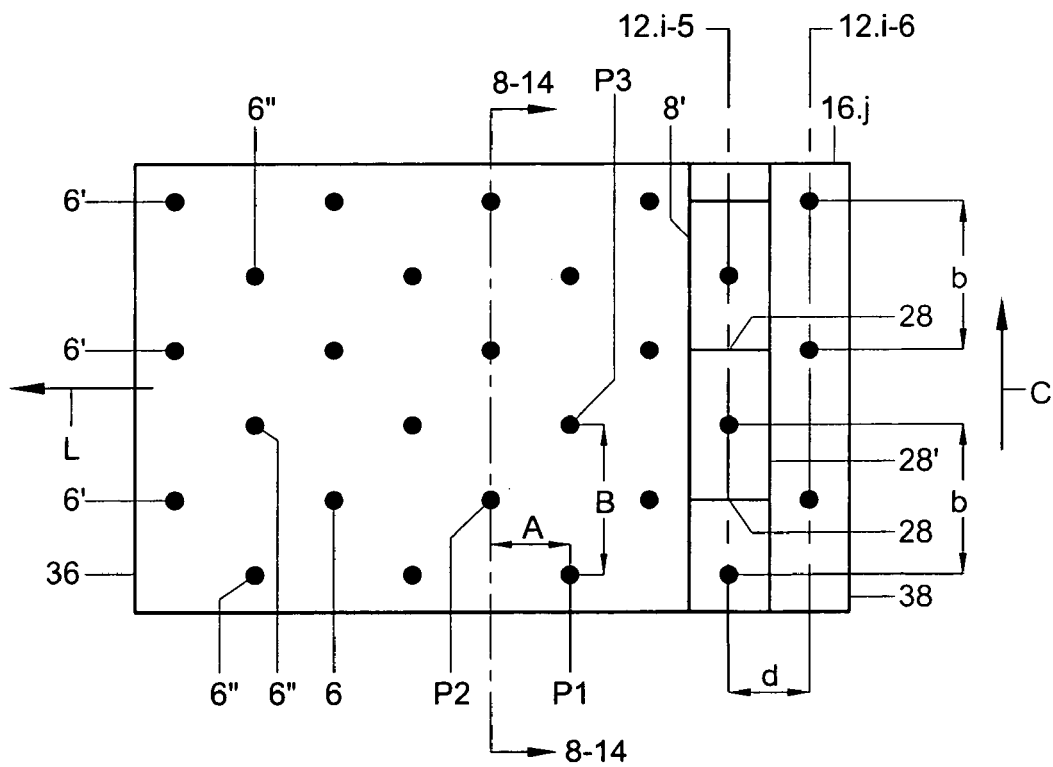
FIG. 6 shows a second embodiment of a wall segment of the apparatus according to FIG. 4 in a direction corresponding to the arrow Pj in FIG. 4.

Hence, the distance between neighbouring pinholes in the direction of the axial axis L also referred to as the z-axis) is smaller than the distance between neighbouring pinholes 6 in a non-axial direction (in this example in the transversal direction C also referred to as the circumferential direction C) The direction L of the axial axis is also referred to as the longitudinal direction L. FIG. 6 shows a wall segment 16.j wherein the pinholes are arranged in an alternative manner relative to each other. Each of the wall segments of the apparatus as shown in FIG. 4 may be provided with the pinhole pattern as shown in FIG. 6. The arrangement of the pinholes in the wall segments 16.j is highly similar as discussed in relation with the apparatus according to FIG. 2. Hence, it also applies for the pinholes of the apparatus according to FIG. 4, which is provided with wall segments 16.j, that the pinholes are arranged in a plurality of flat planes 12.i which planes are at least substantially parallel and separated in the axial direction relative to each other. In this example the planes are each at least substantially perpendicular to the axis L. The normal of the planes may however also include a relatively small angle with said axis L. The distance d between neighbouring planes (see for example the distance d between the planes 12.i–5 and 12.i–6) is smaller than the distance b between neighbouring pinholes within any of such planes (see for example the distance b between neighbouring pinholes laying in the planes 12.i–5 or 12.i–6.

Figure 7:
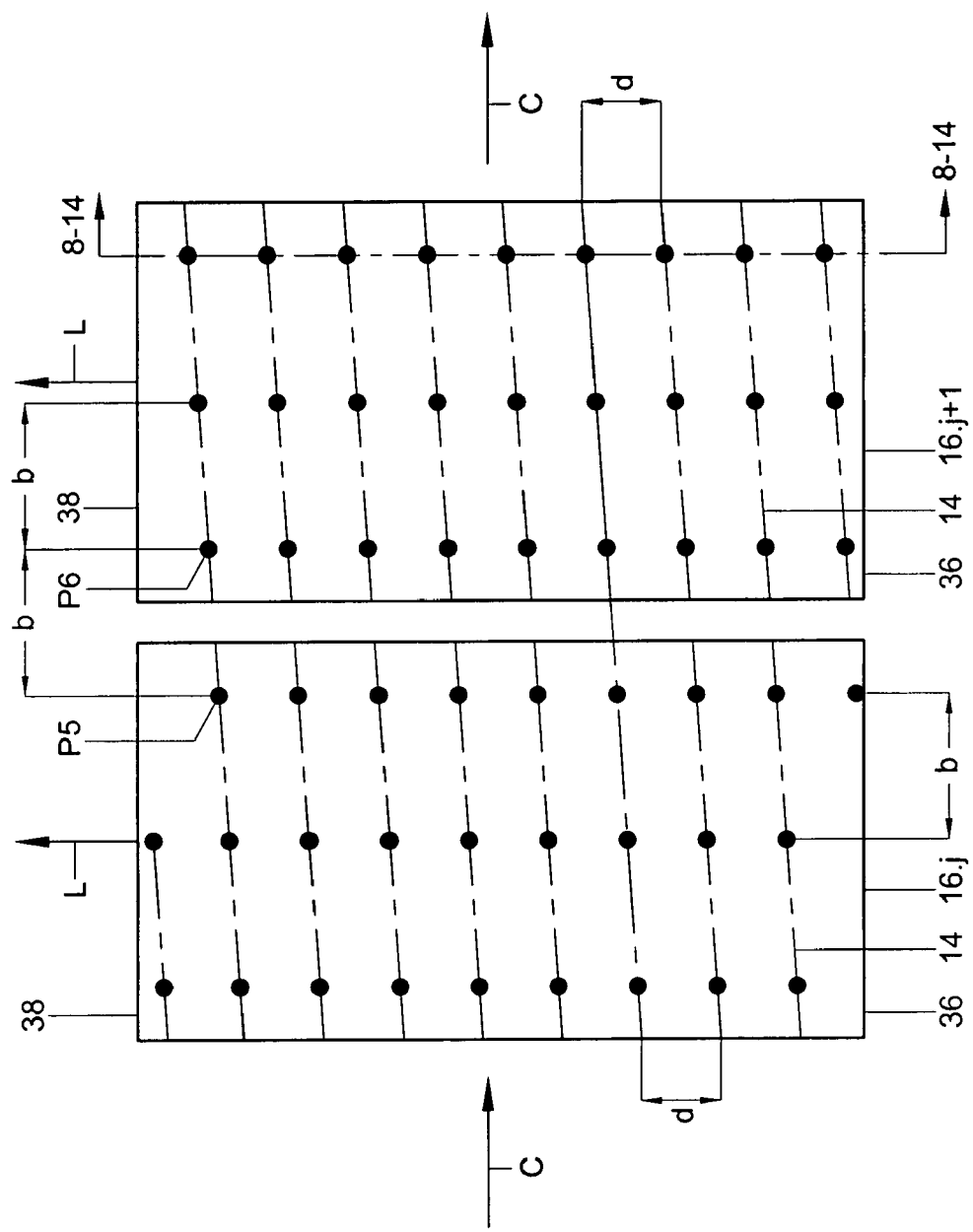
FIG. 7 shows a third possible embodiment of two neighbouring wall segments of the apparatus as shown in FIG. 4 in the directions corresponding with the arrows Pj and Pj+1 as shown in FIG. 4.

In FIG. 7, two neighbouring wall segments 16.j and 16.j+1 are shown. The wall segments 16.j (j=1,2, . . . 8) in combination provide a pattern for the pinholes 6, which is comparable with the pattern according to which the pinholes lay on a helix as discussed in relation with FIG. 3. Again, the pinholes are arranged along the helix 14, which lays in the octagonal surface defined by the eight wall segments 16.j. Hence, the expression "helix" also covers a helix which comprises a plurality of line segments. As can be seen in FIG. 7 the helix 14 is not interrupted between adjacent wall segments 16.j and 16.j+1. For each of the wall segments it applies that the pitch d of the helix is smaller than the distance b between neighbouring pinholes laying on the helix. Although not required by the present invention, this also applies for neighbouring pinholes P5 and P6 laying in different wall segments. However, the distance between neighbouring pinholes laying on different wall segments may, under circumstances, be smaller than the pitch of the helix. Similarly, the distance between neighbouring pinholes laying on different wall segments in accordance with the embodiment discussed in FIG. 5 and 6 may be smaller than the distance between neighbouring surfaces 12.i and 12.i+1.

The pinhole pattern according to FIG. 5 may also be described as follows. An arbitrary first pinhole P1 in a substantially axial direction in relation thereto has a nearest neighbouring pinhole P2 and in a substantially transversal direction has a nearest neighbouring third pinhole P3 wherein the axial component of the distance between the first and second pinholes P1 and P2, respectively, is smaller than the transversal component of the distance between the first and third pinholes P1 and P3 respectively. The same definition applies mutatis mutandis to the embodiments discussed in FIGS. 1–3. The same also applies to the embodiment as discussed in relation with FIG. 6 wherein however the meaning of two neighbouring pinholes P1, P2 which are separated in the substantially axial direction, implies pinholes which are separated in the transversal direction as well whereas the meaning of two neighbouring pinholes P1, P3, which are separated in the transversal direction, implies that these pinholes may not be substantially separated in axial direction as well.

Also shown in FIG. 5 are baffles 28 and 28', which are provided on the wall segment 12.j to prevent undesirable radiation from reaching detector 9.j, as will be explained below.

Each detector 9.j. comprises one or more, in practice at least 3 detector arrays 20, 20', 20". Basically behind each pinhole as viewed from the (axial axis L of the) cavity 2 or lumen of the cavity a detector array 20, 20', 20" is provided (see for example FIGS. 4, 8–12 and 15). Such detector array 20 forms a portion of the detector 9.j. If a polygon with a great number of wall segments is chosen, it is conceivable that in axial direction L each detector 9.j comprises a series of detector arrays 20, one detector array 20 wide. To obtain a particularly good result it is ensured for each pinhole Pi, that radiation passing through the pinhole Pi will fall on each part of the detector array 20 as perpendicularly as possible. That is to say, the detector array 20 is divided into detection elements whose normal is oriented from the middle of an element as much as possible towards the pinhole Pi.

As discussed, FIG. 6 corresponds substantially with FIG. 5, but in a non-axial direction a series of pinholes 6' are staggered in relation to a series of pinholes 6". Thus, any point in the animal A can be viewed from several angles (in the transversal plane), which improves the generation of an accurate tomographic image. As explained below with such a configuration of pinholes and the use of baffles 28', a better reconstruction of the tomographic image is made possible.

As discussed in accordance with a possible embodiment of the invention, FIG. 6 also shows that, for a pinhole $P_1$ having in substantially axial direction a nearest neighbouring pinhole $P_2$ and in substantially transversal direction a nearest third neighbouring pinhole $P_3$, the axial component A of the distance between first and second pinholes $P_1$ and $P_2$, respectively, is smaller than the transversal component B of the distance between the first and the third pinholes $P_1$ and $P_3$, respectively (please note, the orientation of the axial direction is from left to right).

Figure 8:
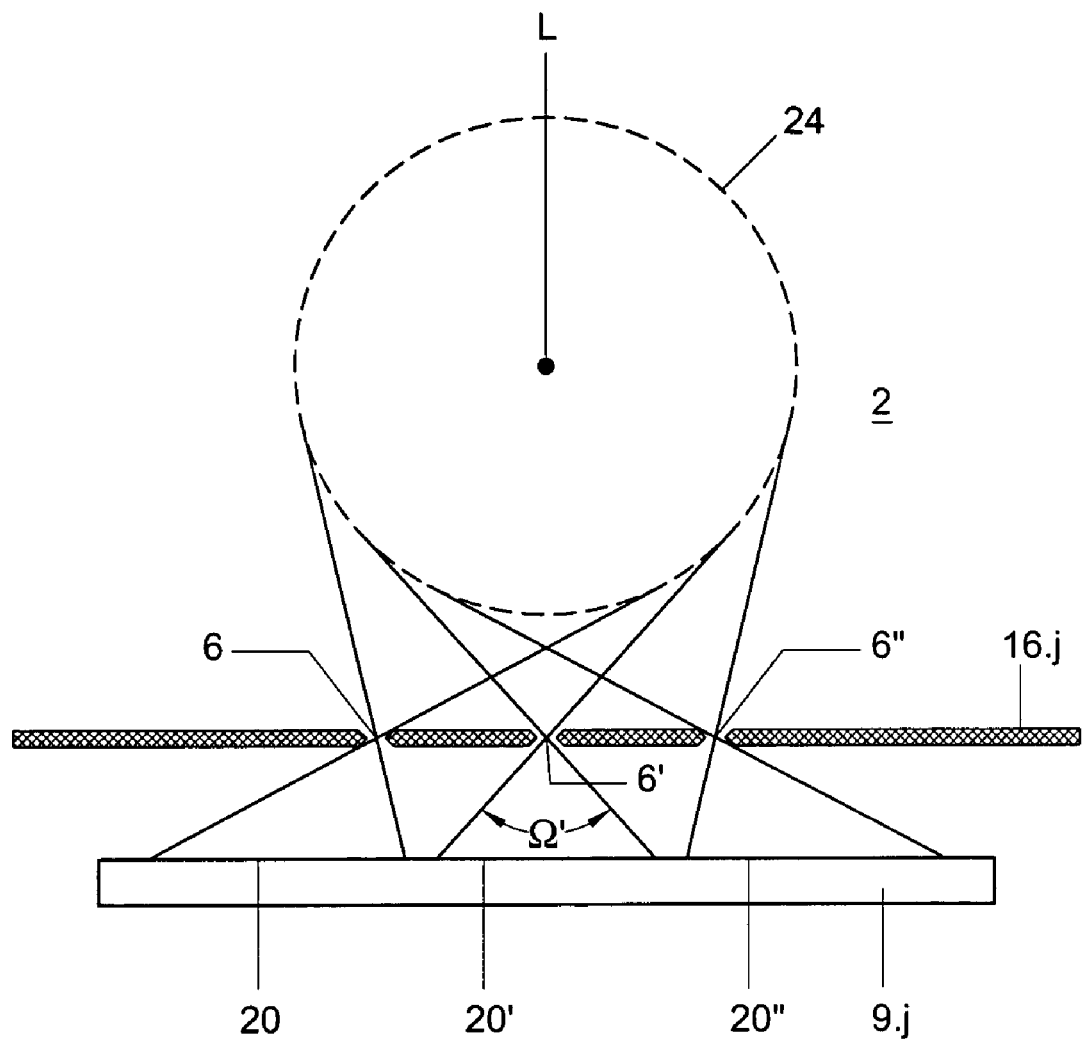
FIG. 8 shows a cross section of a portion of a fourth embodiment of the apparatus according to FIG. 4 in a direction perpendicular to the axial axis of the apparatus.

In FIG. 8 a cross section is shown of a wall segment 16.j of, for example, an apparatus as shown in FIG. 4 in a plane, which is perpendicular to the axis L. The drawing also shows a cross section of a position-sensitive detector 9.j. The wall segment 16.j is again provided with pinholes 6. The pinholes may be provided in a well-known pattern or may be provided in a pattern as discussed in relation with FIGS. 5–7. The detector 9.j is placed so close to the wall segment 16.j that essentially no overlap exists between incident radiation quanta from radioactive non-overlapping projections of area 24 such as can pass the pinholes 6, 6' and 6". The non-overlapping radiation projections through these pinholes define in this example the detector arrays 20, 20' and 20". In this example these detector arrays are adjacent to each other.

Figure 9:
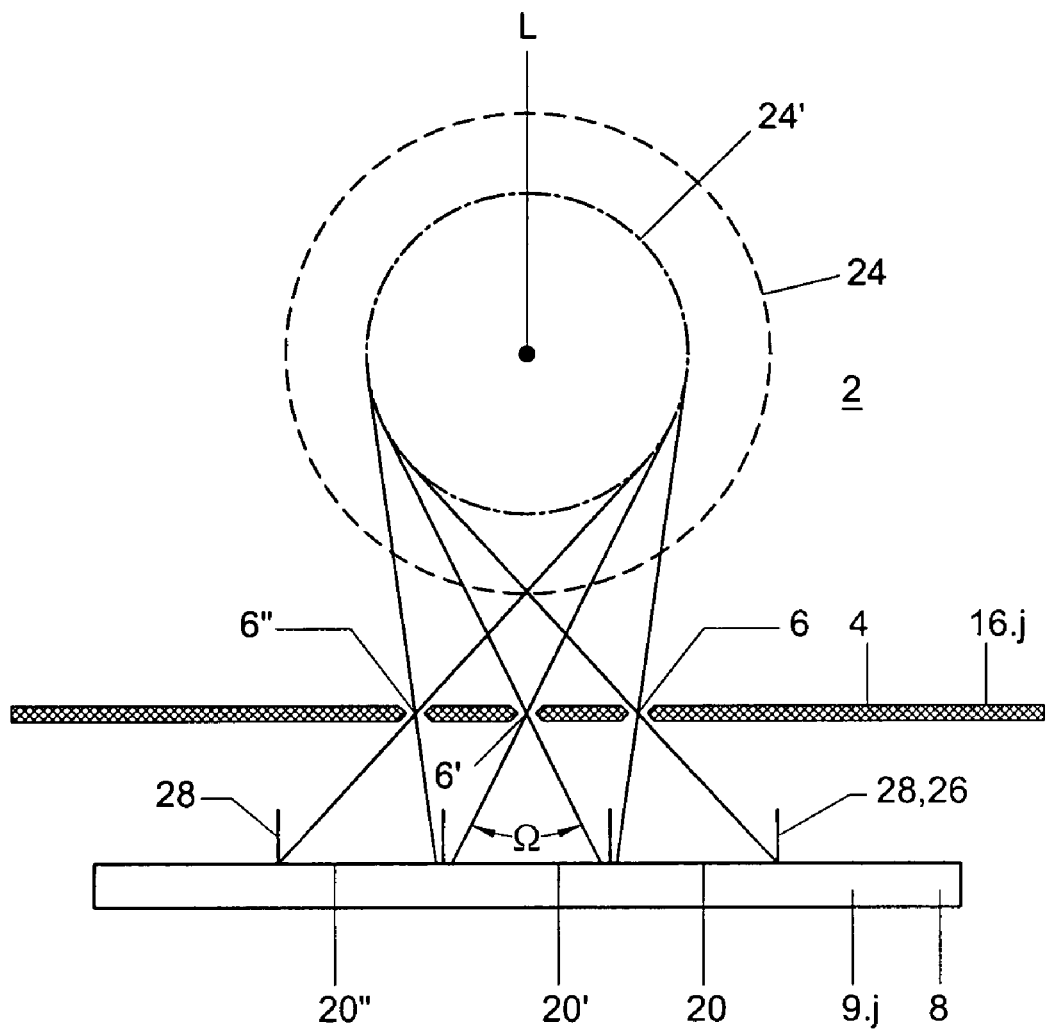
FIG. 9 shows a cross section of a portion of a fifth embodiment of the apparatus according to FIG. 4 in a direction perpendicular to the axial axis of the apparatus.

This can also be realized if the apparatus is further provided with radiation blocking means 26 which partly block radiation which travels from the measuring cavity through at least one of the pinholes to the detection means, in this example the detector 9.j such that the radiation which is detected by the detection means lays in a limited solid angle $\Omega$ relative to the at least one pinhole (see FIG. 9) which is smaller than the solid angle ($\Omega'$) which would have been obtained without the radiation blocking means (see FIG. 8). In the example of FIG. 9, the radiation blocking means 26 comprises baffles 28. In the example given, the baffles 28 are located outside the measuring cavity 2. More specifically, the baffles are arranged between the cavity wall 4 and the detection means 8. In this example the baffles are adjacent to the detection means 8.

In FIG. 9 the baffles 28 prevent radiation passing through a pinhole 6' behind which pinhole 6' a detector array 20' is provided, from reaching an adjacent detector array 20 shifted in a circumferential direction relative to the detector array 20'. According to the embodiment shown in FIG. 9, the baffles 28 are mounted on the position-sensitive detector 9._j_ more specifically between adjacent detector arrays 20 shifted in a circumferential direction relative to each other, and provide a very effective form of radiation shield. Comparing the arrangement of FIG. 8 and FIG. 9 it is clear that the distance between the wall segment 16._j_ and the detector 9._j_ in FIG. 9 is greater than the distance between the wall segment 16._j_ and the detector 9._j_ in FIG. 8. Due to the baffles, which are arranged in FIG. 9 it is prevented that radiation passing through pinhole 6' will reach the detector arrays 20 and 20" and is ensured that said radiation will only reach the detector array 20'. As a result, radiation quanta from the area 24' which is smaller than the area 24, will reach in a non-overlapping way the detector arrays. Hence, the embodiment of FIG. 9 provides a good magnification of the area 24' coupled with a high image resolution.

Figure 10:
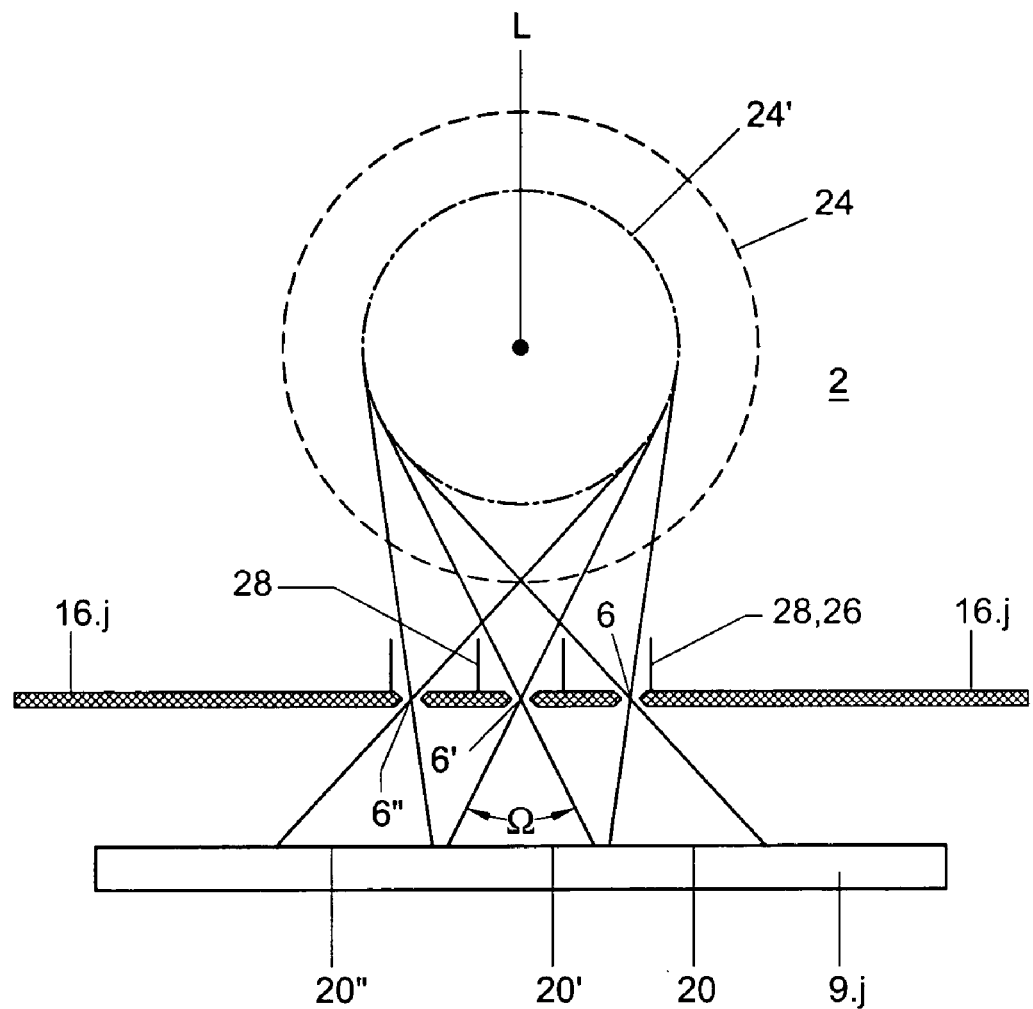
FIG. 10 shows a cross section of a portion of a sixth embodiment of the apparatus according to FIG. 4 in a direction perpendicular to the axial axis of the apparatus.
Figure 11:
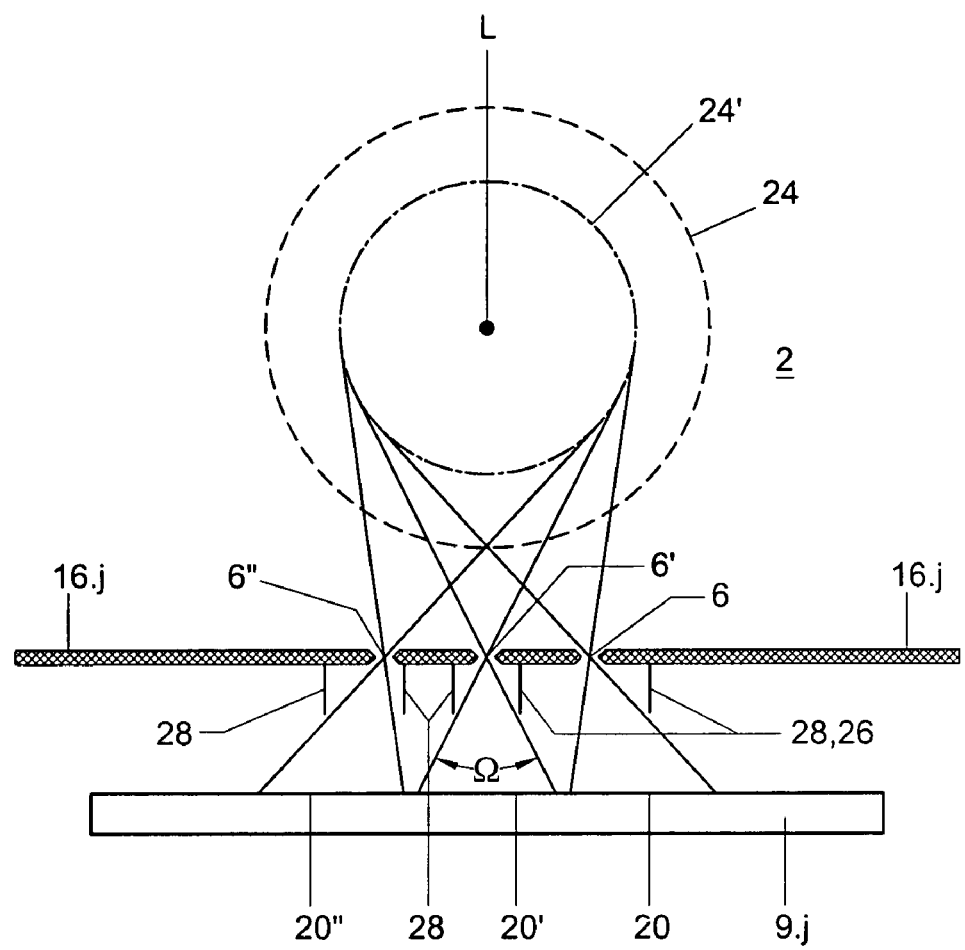
FIG. 11 shows a cross section of a portion of a seventh embodiment of the apparatus according to FIG. 4 in a direction perpendicular to the axial axis of the apparatus.

FIG. 10 shows an embodiment similar to FIG. 9 wherein however the baffles are located inside the measuring cavity 2. More specifically, the baffles 28 are located adjacent to the wall segment 16._j_. The baffles provide the same result as discussed in relation with FIG. 9. In FIG. 11 a similar arrangement as in FIG. 9 is shown wherein however the baffles are located adjacent to the cavity outside the measuring cavity. The embodiment as shown in FIG. 9 has the advantage that it is also possible to vary the distance between the detector 9._j_ and the wall segment 16._j_ which provides a more versatile apparatus.

In the embodiments according to FIGS. 9–11 the baffles may also be placed against the surface of the detector 9._j_ or against the surface of the wall segment 16._j_ without being connected thereto.

Figure 12:
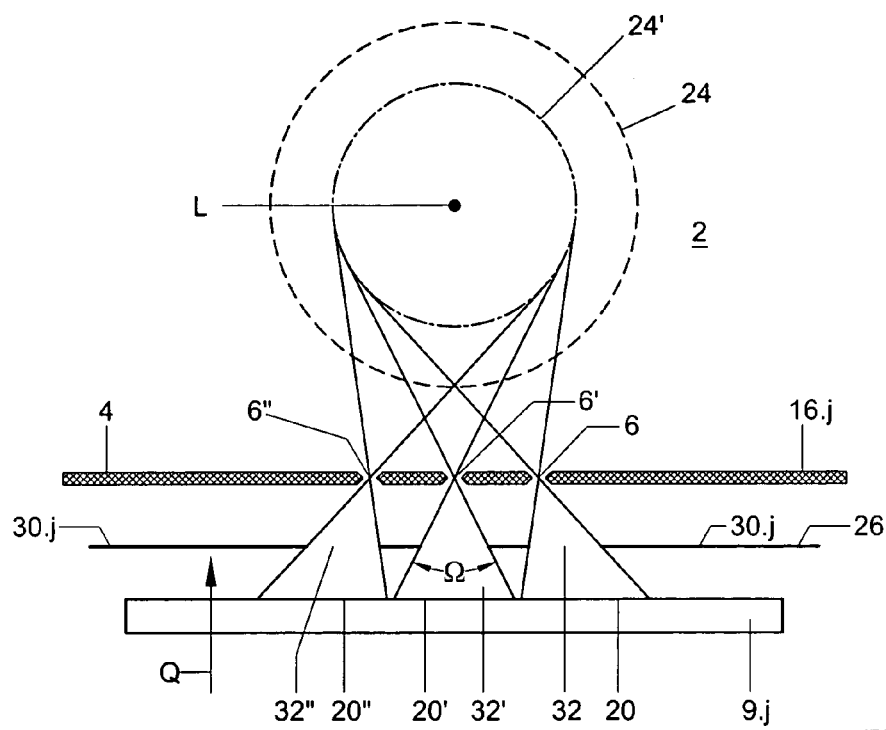
FIG. 12 shows a cross section of a portion of an eighth embodiment of the apparatus according to FIG. 4 in a direction perpendicular to the axial axis of the apparatus.

FIG. 12 shows an alternative embodiment of the invention wherein the apparatus is provided with a radiation blocking means 26 in the form of a blocking wall 30._j_. FIG. 12 shows in this example a wall segment 16._j_ of the apparatus as shown in FIG. 4. It also shows the corresponding detector 9._j_. The blocking wall extends between the cavity wall 4 and the detector 9._j_. The blocking wall comprises a plurality of openings 32, 32', 32" transparent to radiation from respectively the pinholes 6, 6', 6" to the detector 9._j_ laying within said limited solid angle $\Omega$. The blocking wall 30._j_ prevents radiation which passes for example the pinhole 6' and which lays outside the solid angle $\Omega$ to reach the detector array 20" and 20. This radiation will however reach detector array 20'. Hence, the blocking wall 30._j_ provides similar results as discussed in relation with FIGS. 9–12.

Please note that in FIG. 12 only a blocking wall segment 30._j_ is shown which corresponds to the wall segment 16._j_ and the detector 9._j_. It will be clear that similar blocking walls 30._j_ (i=1,2,3, . . . n) will be positioned between each the detector 9._j_ and the corresponding wall segment 16._j_ in FIG. 4 (j=1,2,3, . . . 8).

In the embodiments as shown in FIGS. 9–11, baffles 28 are shown to limit the solid angle in the circumferential direction C. The baffles 28 may be arranged such that the radiation received by one detector array comes from only one pinhole of a series of pinholes which are separated in the circumferential direction C relative to each other.

Baffles 28' may be provided to limit the solid angle $\Omega$ in the axial direction. Examples of an embodiment of an apparatus wherein both baffles 28 as well as baffles 28' are provided are shown in FIGS. 5 and 6. Please note that baffles can be similarly applied to the apparatus as shown in FIG. 1–3 wherein the pattern of the pinholes may be a well-known pattern or the specific patterns as discussed in FIGS. 1–3. The baffles 28' may be arranged such that the radiation received by one detector array comes from only one pinhole of a series of pinholes which are separated in the direction of the axial axis L relative to each other. More generally the baffles 28 and 28' may be arranged such the radiation coming from two different pinholes will not (partially) overlap when received by the detection means 8.

Figures 13, 14:
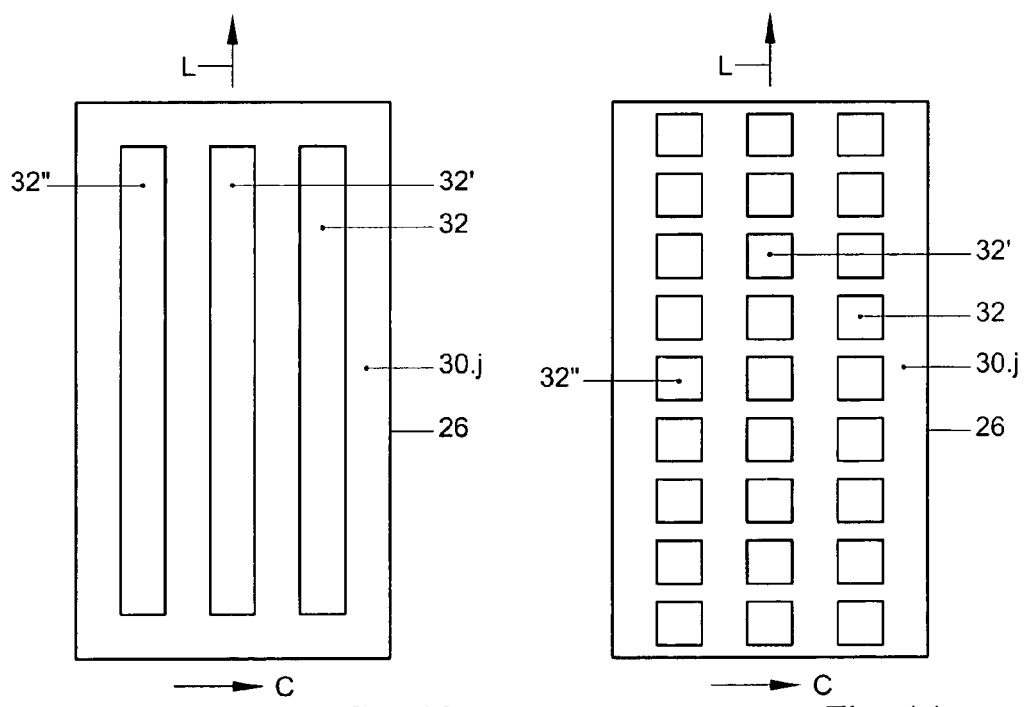
FIG. 13 shows a view of a first embodiment of the blocking wall as shown in FIG. 12.
FIG. 14 shows a second embodiment of the blocking wall as shown in FIG. 12.

An embodiment of a blocking wall 30._j_ as seen in the direction Q (FIG. 12) on the blocking wall 30._j_ is shown in FIG. 13. Please note that for example the opening 32' corresponds with a plurality of pinholes, which are separated in the axial direction from each other. Hence, the opening 32' only provides a limitation of the solid angle in the circumferential direction C. The same applies for the openings 32 and 32" respectively. However, FIG. 14 shows an alternative embodiment of the blocking wall of FIG. 12 viewed in the same direction as discussed for FIG. 13. However, in this case each opening 32 corresponds with one of the pinholes such that the radiation which passes through one of the openings originates from a single one of the pinholes. Hence, in case of the embodiment as shown in FIG. 14 the solid angle is limited by the openings, not only in the circumferential direction C but also in the direction of the axial axis L. Hence, the situation is comparable to the situation discussed previously wherein both baffles 28 as well as baffles 28' are provided.

It will be clear that the baffles 28 and/or 28' as discussed in relation to FIGS. 8–11 may also be used in the apparatuses as discussed in relation to FIGS. 1–3 wherein the pinholes of the apparatuses as discussed for FIGS. 1–3 may also be arranged in any suitable pattern instead of these specific arrangements of the pinholes as discussed for these figures. Also, the apparatus as discussed for FIGS. 1–3 may be provided with a blocking wall 30, which is provided with a plurality of openings 32 for limiting said solid angle per pinhole. Again, the openings may have the form as discussed in relation with FIG. 13 to provide only a limitation of the solid angles in the circumferential direction. The openings may however be possibly arranged as discussed in relation with FIG. 14 so as to limit the solid angle per pinhole in both the circumferential direction C as well as the direction of the axial axis L.

Figure 15:
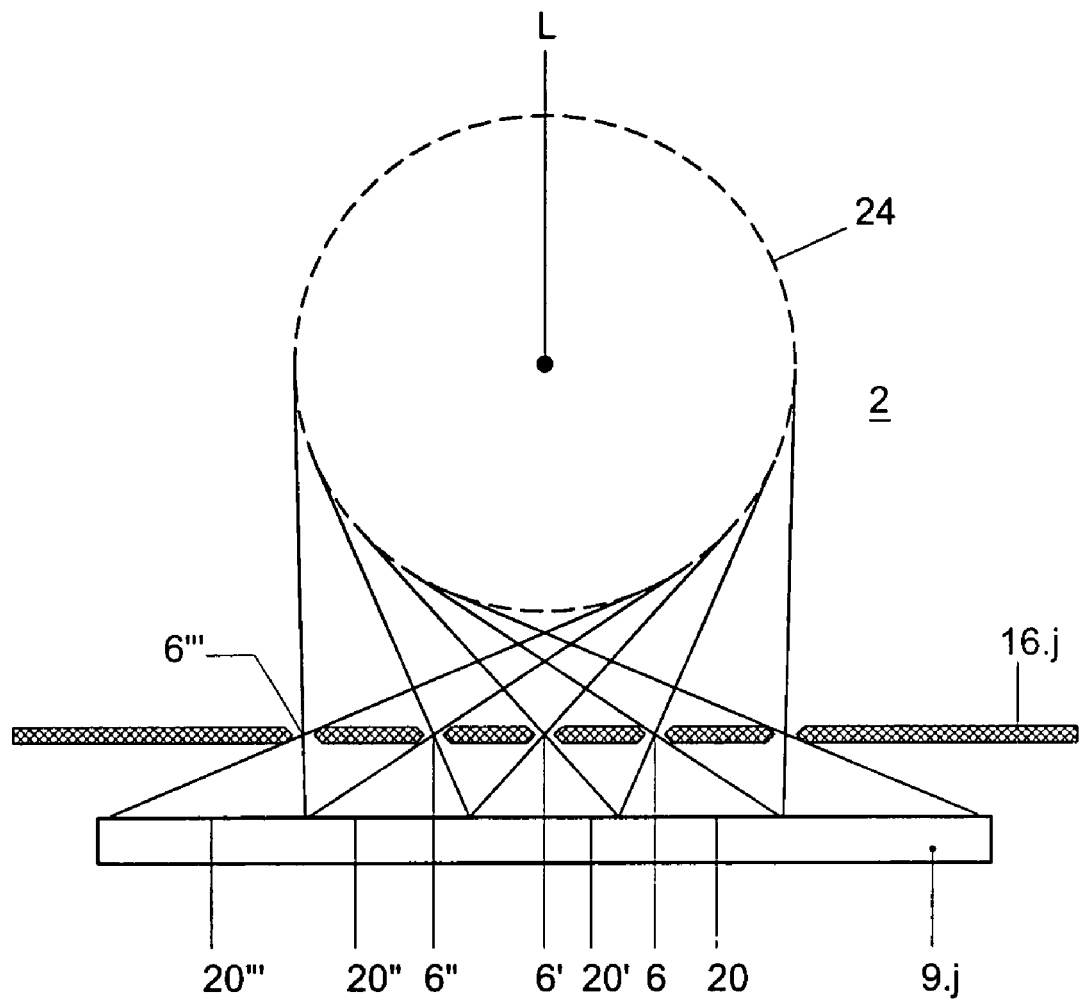
FIG. 15 shows a cross section of a portion of a ninth embodiment of an apparatus according to FIG. 4 in the axial direction of the apparatus

FIG. 15 shows another possible embodiment of a wall segment 16._j_ of an apparatus as, for example, shown in FIG. 4. FIG. 15 shows how, when more than three pinholes are used in the circumferential direction, the distance between the pinholes 6 in the circumferential direction may increase. A person skilled in the art can easily determine a precise positioning such that, for example, a beam of radiation which passes the pinhole 6" can not reach the detection array 20' and the detection array 20''' but can only reach the detection array 20". A possible manner of determining the positions of the pinholes 6 is one departing from an area 24 (which suitably is a round or cylindrical one), within which area the animal (part of the animal) that is to be imaged will be placed. At two sides of this area tangential rays that pass through the pinhole determine the breadth of the radiation projection from the area 24. One single selected pinhole position then determines the position of the other pinholes in order to obtain projections that substantially contact but do not overlap. If the segment 16._j_ is flat and flat position-sensitive detectors are used, the pinholes being removed further from the center of the wall section have to be placed further apart than the pinholes that are closer to the center of the wall section. Hence, if the segment 16._j_ is used in an apparatus as discussed in relation with FIG. 4 and FIGS. 5 and 6, it applies that the distance between two neighbouring pinholes laying in one of said planes or on said helix and laying relatively close to one of the ribs of the polygonal measuring cavity is greater than the distance between two neighbouring pinholes laying in the one of said planes or on said helix and laying substantially in the middle between two adjacent ribs.

In order to obtain the highest possible resolution and high sensitivity, a possible option is to restrict the measuring area 24 (as depicted in FIGS. 8–12 and 15), i.e. to reduce its diameter. This results in the measuring area 24'. Hence, these are advantages obtained within a limited volume of the measuring cavity. By performing a translation in a transversal plane, it is possible to also measure another area of the animal with that improved resolution and sensitivity. The use of baffles 28 or a blocking wall in accordance with the invention, allows pinholes to be positioned very closely together, not only in axial direction but also in the circumferential direction so that a high sensitivity can be achieved, and in addition an excellent resolution, not only in the axial direction.

Furthermore, in each of the embodiments discussed in relation to FIGS. 4–15 it may be that the (axis of the) bore of the pinholes located near to the ribs 33 of the polygonal measuring cavity is at an angle to the normal 34 of the wall segment 16.j thereby pointing in a direction of the axial axis L. The direction 41 of such bore is shown in FIG. 4 as a possible example. In addition or alternatively the bore of the pinholes situated near the axial ends 36, 38 may be provided at an angle $\beta$ to the normal 34 of the wall segment 9.j thereby pointing in a direction of the absolute center 40 of the measuring cavity. The direction 42 of such a bore is shown in FIG. 2b as a possible example. Please note that such a direction of the bores of the pinholes may be used in each of the embodiments as previously discussed. It is also possible that the respective pinholes situated nearer the axial ends 36, 38 of the measuring cavity may be at an angle to the respective normals of the wall segment near said respective pinholes thereby at least substantially pointing in the direction of a line segment 39 at least substantially extending through the absolute center 40 of the measuring cavity in the direction of the axial axis L wherein said line segment is substantially shorter than the length M of the measuring cavity in the axial direction, for example shorter than 50%, preferably shorter than 30% and more preferably shorter than 15% of the length of the measuring cavity in the axial direction.

Figure 16:
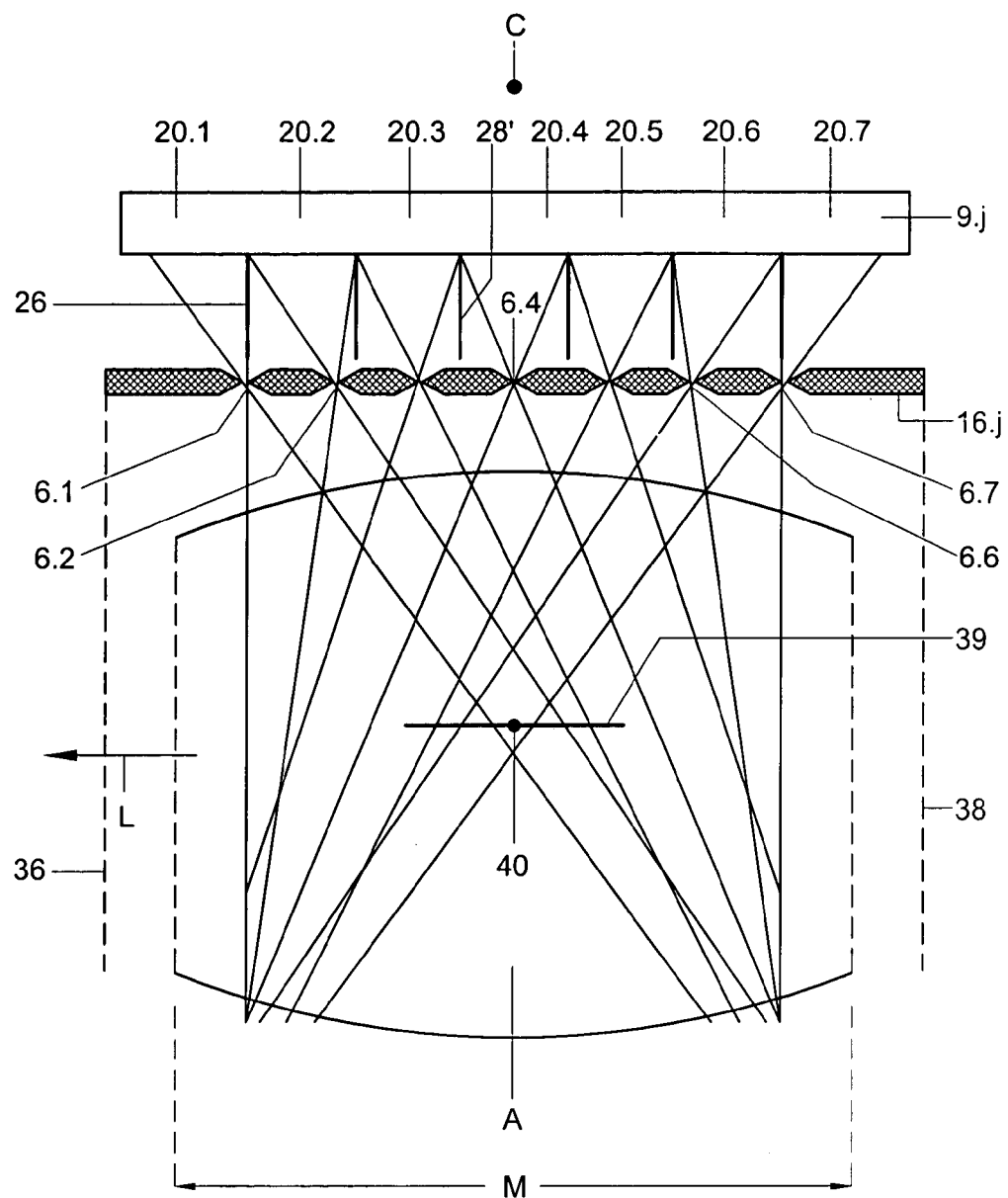
FIG. 16 shows a cross section of a portion of an eleventh embodiment of an apparatus according to FIG. 4 in the axial direction of the apparatus.

FIG. 16 shows a cross section in the axial direction L of a possible embodiment of a portion of the apparatus as shown in FIG. 4. In this embodiment the axe of each one of the pinholes 6.1 and 6.7 can form an angle with the axe of each one of the pinholes 6.2–6.6. There are various manners of directing. For example the respective pinholes 6.1, 6.7 situated nearer the axial ends 36, 38 of the measuring cavity may be at an angle to the respective normals of the wall segment near the respective pinholes thereby at least substantially pointing in the direction of the absolute center (or heart) 40 of the measuring cavity or in the direction of a line segment 39 at least substantially extending through the absolute center 40 of the measuring cavity in the direction of the axial axis L wherein said line segment is substantially shorter than the length M of the measuring cavity in the axial direction, for example shorter than 50%, preferably shorter than 30% and more preferably shorter than 15% of the length of the measuring cavity in the axial direction According to the illustrated embodiment baffles 28' are provided that restrict the path of the beam from particular angles through a pinhole, so that a directing effect is obtained. In other words, the baffles 28' prevent for example radiation via pinhole 6.4 from reaching the detector arrays 20.1–20.3 and 20.5–20.7 and do not prevent that said radiation is received by the detector array 20.4. The baffles 28' are arranged such that the radiation received by one detector array 20.i (i=1,2, . . . or 7) comes from only one pinhole from a series of adjacent pinholes which are shifted in the direction of the axial axis L relative to each other. In this way the animal A, such as a human, or a part of the body, such as a head, can be viewed from more angles, which facilitates the reconstructability and increases sensitivity for an area in the body. In an embodiment as shown in FIGS. 1–3 the pinholes may be directed by means of the curve of the wall 4, catching radiation more effectively, which further increases the sensitivity. Especially for the example of FIG. 4, it is advantageous for the pinholes 6 to be provided in, for example, a cylindrical body, and for wall segments 16.j to be provided with drillings (positioned at various angles) into which the cylindrical bodies are inserted.

Pinholes 6 may be unround, for example, oval or rectangular, with the longitudinal axis preferably oriented in transversal direction.

As shown in FIG. 6, axially successive series of pinholes 6 arranged substantially in transversal direction C are, according to an interesting variant, staggered in relation to one another. By moving the object to be measured in the axial direction in relation to the measuring cavity, it is thus possible after the movement, to view a particular segment of the object under a different angle. In this way, a higher resolution can be obtained. On the basis of the radiation energy or on the basis of a statistical distribution thereof, it is also possible to obtain more information with respect to the precise location of a radiation source in the measuring cavity.

If detector 9.j can determine the energy of gamma or X-ray photons, it is possible to differentiate between scattered radiation and direct radiation, and to reject the improperly detected scattered photons.

Figure 17A:
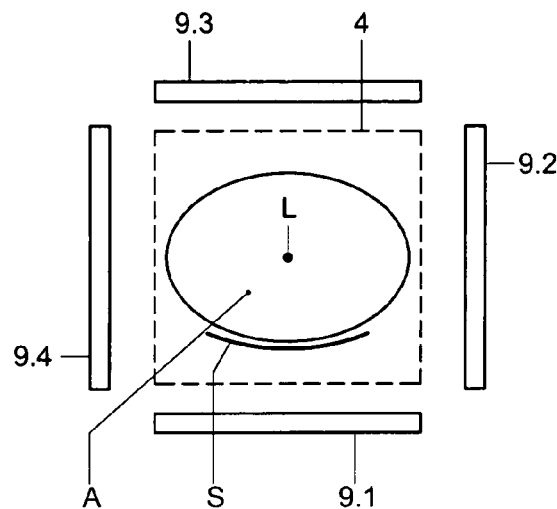
FIGS. 17a and 17b show a cross section of an eleventh embodiment of an apparatus according to the invention in a direction perpendicular to an axial axis of the apparatus.
Figure 17B:
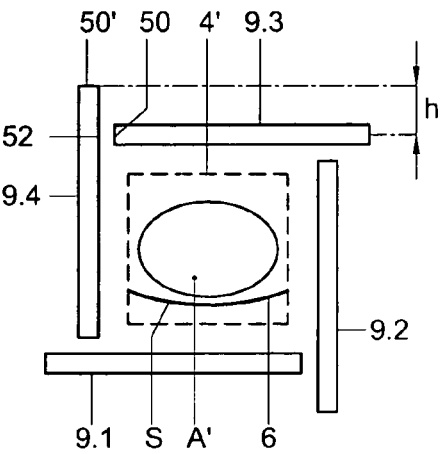

In FIGS. 17a and 17b a possible embodiment of an apparatus according to the invention is shown which (in this case) has four flat detectors 9.j (j=1,2,3,4). The four detectors 9.j can be moved in relation to one another. A first arrangement of the positions of the detectors 9.j relative to each other is shown in FIG. 17a whereas a second arrangement of the position of the four detectors 9.j relative to each other is shown in FIG. 17b. It shows that in both cases the position-sensitive detectors 9.j form a surrounding surface of position-sensitive detectors having a circumference that may be varied. In case of FIG. 17b the circumference is smaller than the sum of all the widths of the position-sensitive detectors. The cavity wall 4 in FIG. 17a may be replaced by a cavity wall 4' which is smaller. However, the position sensitive detectors 9.j, which are used in FIGS. 17a and 17b are the same. This provides a flexible apparatus in which both large animals as well as small animal 3' can be measured. Hence, the only thing which has to be replaced is the cavity wall 4 for defining to the cavity 2. This cavity wall 4 may in each case comprise four wall segments 16.j (j=1,2,3,4). Hence, for the apparatus as shown in FIGS. 17a and 17b this means that the detection means 8 is divided into, in this example, four at least substantially flat detectors 9.j wherein an edge 50 directed in the direction of the axial axis L of at least one of the wall detectors 9.j is adjacent to a selectable portion 52 of a neighbouring detector 9.j+1, 9.j−3 said portion 52 being directed in the direction of the axial axis L and being directed to (facing) the measuring cavity 2 so that the diameter of the space, which is at least partially surrounded by the detection means, can be varied by selecting the distance h between said portion 52 of said neighbouring detector 9.*j*+1, 9.*j*–3 and an edge 50' directed in the direction of the axial axis L of said neighbouring detector 9.*j*.

Figure 17C:
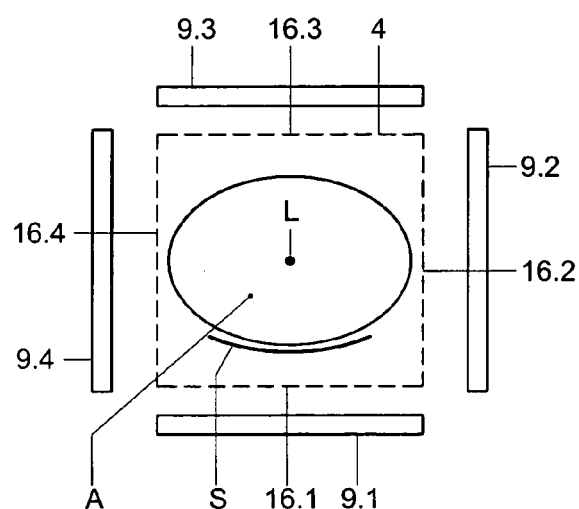
FIGS. 17c and 17d a cross section of a twelfth embodiment of an apparatus according to the invention in a direction perpendicular to an axial axis of the apparatus.
Figure 17D:
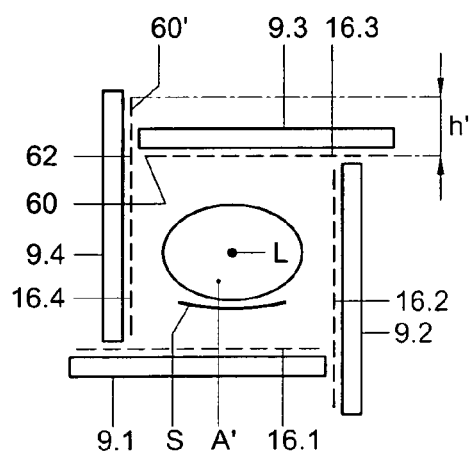

As discussed in the apparatus according to FIGS. 17*a* and 17*b* the cavity wall as shown in FIG. 17*a* has to be replaced by a cavity wall 4' as shown in FIG. 17*b*. This can however also be prevented. This is shown in FIGS. 17*c* and 17*d* respectively. In the embodiment as shown in FIG. 17*a*, the cavity wall 4 in the apparatus according to FIGS. 17*c* and 17*d* and the position sensitive detectors 9.*j* can be re-arranged relative to each other as discussed in relation with FIGS. 17*a* and 17*b*. However, the cavity wall 4 comprises in this case four flat wall segments 16.*j* which each are provided with a plurality of pinholes 6. The wall segments 16.*j* can be re-arranged relative to each other in a similar fashion as discussed for the detectors 9.*j*. Hence, it holds that for the embodiment as shown in FIGS. 17*c* and 17*d* that an edge 60 directed in the direction of the axial axis L of at least one of the wall segments 16.3 is adjacent to a selectable portion 62 of a neighbouring wall segment 9.4 said portion 62 being directed in the direction of the axial axis L and being directed to (facing) the measuring cavity 2 so that the diameter of the measuring cavity 2 can be varied by selecting the distance h' between said portion 62 of said neighbouring wall segment 16.4 and an edge 60' directed in the direction of the axial axis L of said neighbouring wall segment 16.4.

Of course, it is also possible that only the wall segments 16.*j* can be re-arranged to each other as discussed, wherein the detection means 8 are however fixed.

If the apparatus is provided with a blocking wall 30, the blocking wall may also comprise blocking wall segments, similar as discussed in relation with the cavity wall 4. In that case the diameter of a space 78 which is at least partially surrounded by the blocking wall 30 and which space comprises the measuring cavity 2 and the cavity wall 4 may be varied similar as discussed in relation with the cavity wall 4 in FIGS. 17*c* and 17*d*. This is shown in FIGS. 17*e* and 17*f* respectively. In the embodiment as shown in FIGS. 17*e* and 17*f* the position sensitive detectors 9.*j* can be re-arranged relative to each other as discussed in relation with FIGS. 17*a* and 17*b*. However, the blocking wall 30 comprises in this case four flat wall segments 30.*j* which each are provided with a plurality of openings 32. The blocking wall segments 30.*j* can be re-arranged relative to each other in a similar fashion as discussed for the detectors 9.*j*. Hence, it holds that for the embodiment as shown in FIGS. 17*e* and 17*f* that an edge 80 directed in the direction of the axial axis L of at least one of the wall segments 30.3 is adjacent to a selectable portion 82 of a neighbouring wall segment 30.4 said portion 82 being directed in the direction of the axial axis L and being directed to (facing) the measuring cavity 2 so that the diameter of the space 78 can be varied by selecting the distance h" between said portion 82 of said neighbouring wall segment 30.4 and an edge 80' directed in the direction of the axial axis L of said neighbouring wall segment 30.4.

Of course, it is also possible that only the wall segments 30.*j* can be re-arranged to each other as discussed, wherein the detection means 8 are however fixed. Also the cavity wall may or may not be varied according to the two possibilities as discussed for FIGS. 17*a*–17*d*.

In each of the embodiments as discussed, in use, the cavity wall 4 is stationary relative to the detecting means 8.

The application of a radioactive compound or composition to an animal and the generation of a tomographic image, which includes a three-dimensional image constructed from tomographic images obtained from measuring data is within the general knowledge of a person skilled in the art and requires no further explanation.

The animal to be measured by means of an apparatus may also be a human. The apparatus is in particular also suitable for small mammals such as mice or rats. Measurements of parts of an animal may include examinations of brain and heart.

The baffles 28, 28' may be provided with radiation-absorbent and/or—reflecting elements. Some possible embodiments of these are illustrated in FIG. 18. These elements may help to prevent radiation quanta being scattered on the wall and due to scattering falling on inappropriate detection means. Even if that does happen, the fact that due to scattering the radiation quantum has lost energy makes it possible for such radiation quanta that cause noise to be filtered out by using a detection means that measures the radiation energy. One example of such a detection means is a CdZnTe detector array.

The invention is in no way limited to the above referred to special embodiments. Hence, for example the embodiments of the wall segments and/or detection means which are discussed on the basis of FIG. 4 and FIG. 17, may also be used in other apparatuses comprising a different number of wall segments and/or detectors. Furthermore the pinholes 6 may be filled with a material, which does not black the radiation. The same applies to the openings 32 of the blocking walls 30.*j*. or the blocking wall 30.

Also the cavity wall 4 may be arranged to be replaceable by another cavity wall comprising other dimensions and/or other patterns of pinholes and/or pinholes having other dimensions. For example in FIG. 4 the cylinder cavity wall 4 may be replaced by a cylinder cavity wall having a smaller or greater diameter for varying the dimensions of the cavity 2 and/or the distance between the cavity wall and the detection means 8. Also the patterns of pinholes and/or dimensions of pinholes may thus be varied. Similarly the wall segments 16.*j* may be replaced by other wall segments having a greater or smaller surface and/or having other pinhole patterns and/or pinholes having other dimensions.

Also the blocking wall 30 may be arranged to be replaceable by another blocking wall comprising other dimensions and/or other patterns of openings 32 and/or openings 32 having other dimensions. For example in FIG. 4 the cylinder blocking wall 30 may be replaced by a cylinder blocking wall having a smaller or greater diameter for varying the distance between the cavity wall and the blocking wall and/or the distance between the blocking wall and the detection means 8. Also the pattern of the openings and/or the dimensions of the openings 32 may thus be varied. Similarly the blocking wall segments 30 may be replaced by other blocking wall segments having a greater or smaller surface and/or having other opening patterns and/or openings 32 with other dimensions.

According to the invention at least one of the baffles is retractable so that, in use, the retracted baffle will not be illuminated by the radiation from the cavity. Hence this means that in each of the embodiments comprising baffles at least one of the baffles may be removed from the apparatus or be moved to another position in the apparatus so that, in use, the retracted baffle will not be illuminated by the radiation from the cavity. For example at least one, some or each of the baffles 28 and/or the baffles 28' may be retractable. This may be useful if an image of a small object such as a tumor has to be obtained.

Such variations all fall within the scope of the present invention.

The invention claimed is:

1. A method of obtaining a tomographic image of part of an animal or a part of an animal including a human being or a part of a human being by using radioactive radiation, wherein the animal is at least partly placed into a measuring cavity having an axial axis, the measuring cavity being at least partially surrounded by a cavity wall which is provided with a plurality of pinholes, and wherein behind the pin holes (as viewed from the measuring cavity) detection means are placed, radioactive radiation from a radioactive isotope administered to the animal is detected in a position-related manner by the detection means and data obtained with the detection means are used for the generation of the tomographic image, wherein:

the pinholes are at least substantially arranged in a plurality of flat planes which planes are at least substantially parallel and separated in the direction of the axial axis relative to each other wherein the distance between neighboring planes is smaller than the distance between neighboring pinholes within such a plane wherein distance between neighboring planes is at least 1.03, at least 1.05, at least 1.3, more specifically at least 2, preferably at least 5 or more preferably a least 10 times smaller than the distance between neighboring pinholes within any of such planes; or the pinholes are at least substantially arranged along a helix wherein the pitch of the helix is generally smaller than the distance between neighboring pinholes laying on the helix wherein the pitch of the helix is generally at least 1.03, at least 1.05, at least 1.3, more specifically at least 2, preferably at least 5 or more preferably at least 10 times smaller than the distance between neighboring pinholes laying along the helix.

2. An apparatus for obtaining a tomographic image of a human being or part of a human being or an animal or a part thereof using radioactive radiation, which apparatus comprises a measuring cavity having an axial axis, a cavity wall which at least partly surrounds the measuring cavity which cavity wall is provided with a plurality of pinholes, the apparatus further comprising detection means which viewed from the cavity, are provided behind the pin holes, wherein the detection means are arranged for receiving, in a position-related manner, the radioactive radiation emitted within the measuring cavity and wherein the detection means can be read electronically or optically, wherein:

the pinholes are at least substantially arranged in a plurality of flat planes which planes are at least substantial parallel and separated in the direction of the axial axis relative to each other wherein the distance between neighboring planes is smaller than the distance between neighboring pinholes within any of such planes wherein distance between neighboring planes is at least 1.03, at least 1.05, at least 1.3, more specifically at least 2, preferably at least 5 or more preferably a least 10times smaller than the distance between neighboring pinholes within any of such planes; or the pinholes are substantially arranged along a helix wherein the pitch of the helix is generally smaller than the distance between neighboring pinholes laying on the helix wherein the pitch of the helix is generally at least 1.03, at least 1.05, at least 1.3, more specifically at least 2, preferably at least 5 or more preferably at least 10 times smaller than the distance between neighboring pinholes laying along the helix.

3. An apparatus according to claim 2, wherein the cavity wall is of a rotationally symmetrical design around the axial axis of the measuring cavity.

4. An apparatus according to claim 3, wherein the cavity wall has a shape of a cylinder.

5. An apparatus according to claim 3, wherein the cavity wall has a polygonal cross section in a direction perpendicular to the axial axis.

6. An apparatus according to claim 5, wherein polygonal cross section comprises n angles (n greater than or equal to 3).

7. An apparatus according to claim 6, wherein the cavity wall comprises a number of at least substantially flat wall segments having the pinholes.

8. An apparatus according to claim 7, wherein the cavity wall comprises n wall segments.

9. An apparatus according to claim 7, wherein the wall segments have a rectangular shape.

10. An apparatus according to claim 9, wherein pinholes that are located relatively close to the ribs of the polygonal measuring cavity are at an angle to the normal of the wall segment, thereby pointing in the direction of the axial axis.

11. An apparatus according to claim 10, wherein the distance between two neighboring pinholes laying in one of said planes or on said helix and laying relatively close to one of the ribs of the polygonal measuring cavity is greater than the distance between two neighboring pinholes laying in the one of said planes or on said helix and laying substantially in the middle between two adjacent ribs.

12. An apparatus according to claim 11, wherein respective pinholes situated nearer the axial ends of the measuring cavity are at an angle to the normals of the wall segment near the respective pinholes thereby at least substantially pointing in the direction of the absolute center of the measuring cavity or in the direction of a line segment at least substantially extending through the absolute center of the measuring cavity in the direction of the axial axis wherein said line segment is substantially shorter than the length of the measuring cavity in the direction of the axial axis, for example shorter than 50%, preferably shorter than 30% and more preferably shorter than 15% of the length of the measuring cavity in the direction of the axial axis.

13. An apparatus according to claim 12, wherein an edge directed in the axial direction of at least one of the wall segments is adjacent to a selectable portion of a neighboring wall segment said portion being directed in the direction of the axial axis and being directed to the measuring cavity so that the diameter of the measuring cavity can be varied by selecting the distance between said portion of said neighboring wall segment and an edge directed in the direction of the axial axis of said neighboring wall segment and/or that the detection means comprises a plurality of substantially flat detectors wherein an edge directed in the direction of the axial axis of at least one of the detectors is adjacent to a selectable portion of a neighboring detector said portion being directed in the direction of the axial axis and being directed to the measuring cavity so that the diameter of a cavity formed by the detectors can be varied by selecting the distance between said portion of said neighboring wall detector and an edge directed in the direction of the axial axis of said neighboring detector.

14. An apparatus according to claim 13, wherein the apparatus is further provided with radiation blocking means which partly block radiation which travels from the measuring cavity through at least one of the pinholes to the detection means such that the radiation which is detected by the detection means lays in a limited solid angle relative to the at least one pinhole, which angle is smaller than the solid angle which would have been obtained without the radiation blocking means.

15. An apparatus according to claim 14, wherein the detection means comprises a plurality of detector arrays wherein the radiation blocking means are arranged such that each detection array only receives radiation coming from one of the pinholes.

16. An apparatus according to claim 15, wherein the radiation blocking means comprises baffles.

17. An apparatus according to claim 16, wherein the baffles are located inside the measuring cavity.

18. An apparatus according to claim 17, wherein the baffles are located adjacent the cavity wall.

19. An apparatus according to claim 16, wherein the baffles are located outside the measuring cavity.

20. An apparatus according to claim 19, wherein the baffles are arranged between the cavity wall and the detection means.

21. An apparatus according to claim 20, wherein the baffles are adjacent the cavity wall.

22. An apparatus according to claim 20, wherein the baffles are adjacent the detection means.

23. An apparatus according to claim 22, wherein the baffles each lay substantially in a plane through said axial axis.

24. An apparatus according to claim 23, wherein the baffles are provided with projecting elements having a direction component parallel to a surface of the detection means.

25. An apparatus according to claim 14 wherein the radiation blocking means comprise a blocking wall extending between the cavity wall and the detection means wherein said blocking wall comprises a plurality of openings for providing a passage for the radiation from the pinholes to the detection means laying within said limited solid angle.

26. An apparatus according to claim 25, wherein the openings of the blocking wall have a surface which is greater than the surface of the pinholes.

27. An apparatus according to claim 25, wherein each opening of the blocking wall corresponds with one of the pinholes such that the radiation which passes through one of the openings comes from a single one of the pinholes.

28. An apparatus according to claim 27, wherein the blocking wall has a shape which is substantially similar to the shape of the cavity wall.

29. An apparatus according to claim 28, wherein the blocking wall comprises at least substantially flat wall segments having the openings wherein an edge directed in the direction of the axial axis of at least one of the wall segments is adjacent to a selectable portion of a neighboring wall segment said portion being directed in the direction of the axial axis and being directed to the measuring cavity so that the diameter of a space which is at least partly surrounded by the blocking wall and which space comprises the measuring cavity can be varied by selecting the distance between said portion of said neighboring wall segment and an edge directed in the direction of the axial axis of said neighboring wall segment.

30. An apparatus according to claim 29, wherein the blocking wall is of a rotationally symmetrically design around the axial axis of the measuring cavity.

31. An apparatus according to claim 30, wherein the blocking wall has a polygonal cross section in a direction perpendicular to the axial axis.

32. An apparatus according to claim 31, wherein polygonal cross section comprises n angles (n greater than or equal to 3).

33. An apparatus according to claim 32, wherein the blocking wall comprises n wall segments and/or that the detection means comprises n detectors.

34. An apparatus according to claim 2, wherein the distance between neighboring planes is not smaller than 0.03 and preferably 0.05 times the distance between neighboring pinholes within any of such planes.

35. An apparatus according to claim 2, wherein the distance between neighboring planes is 0.03–0.98 and more preferably 0.05–0.77 times the distance between neighboring pinholes within any of such planes.

36. An apparatus according to claim 2, wherein the pitch of the helix is not smaller than 0.03 and preferably 0.05 times the distance between neighboring pinholes laying on the helix.

37. An apparatus according to claim 2, wherein the pitch of the helix is 0.03–0.98 and more preferably 0.05–0.77 times the distance between neighboring pinholes laying on the helix.

38. An apparatus for obtaining a tomographic image of a human being or part of a human being or an animal or a part thereof using radioactive radiation, which apparatus comprises a measuring cavity having an axial axis, a cavity wall which at least partly surrounds the measuring cavity which cavity wall is provided with a plurality of pinholes, the apparatus further comprising detection means which viewed from the cavity, are provided behind the pinholes, where the detection means are arranged for, in a position-dependent manner, the detection of radioactive radiation emitted within the measuring cavity and the detection means can be read electronically or optically, wherein the cavity wall comprises at least substantially flat wall segments having the pinholes wherein an edge directed in the direction of the axial axis of at least one of the wall segments is adjacent to a selectable portion of a neighboring wall segment said portion being directed in the direction of the axial axis and being directed to the measuring cavity so that the diameter of the measuring cavity can be varied by selecting the distance between said portion of said neighboring wall segment and an edge directed in the direction of the axial axis of said neighboring wall segment and/or wherein the detection means comprises a plurality of substantially flat detectors wherein an edge, directed in the direction of the axial axis, of at least one of the detectors is adjacent to a selectable portion of a neighboring detector said portion being directed in the direction of the axial axis and being directed to the measuring cavity so that the diameter of a cavity formed by the detectors can be varied by selecting the distance between said portion of said neighboring wall detector and an edge directed in the direction of the axial axis of said neighboring detector, wherein the cavity wall is of a rotational symmetrical design around the axial axis of the measuring cavity and wherein the cavity wall has a polygonal cross section in a direction perpendicular to the axial axis.

39. An apparatus according to claim 38, wherein the polygonal cross section comprises n angles (n greater than or equal to 3).

40. An apparatus according to claim 39, wherein the cavity wall comprises n wall segments and/or that the detection means comprises n detectors.

41. An apparatus according to claim 40, wherein pinholes that are located nearer the ribs of the polygonal measuring cavity are at an angle to the normal of the wall segment in the direction of the axial axis.

42. An apparatus according to claim 41, wherein pinholes laying substantial in a plane perpendicular to the axial axis and being near one of the ribs of the polygonal measuring cavity are spaced further apart than pinholes laying substantial in the plane perpendicular to the axial axis and laying substantial in the middle between two adjacent ribs.

43. An apparatus according to claim 42, wherein pinholes situated relatively close to the axial ends of the measuring cavity are at an angle to the normal of the wall segment in the direction of the absolute centre of the measuring cavity.

44. An apparatus according to claim 43, wherein the wall segments have a rectangular shape.

45. An apparatus for obtaining a tomographic image of a human being or part of a human being or an animal or a part thereof using radioactive radiation, which apparatus comprises a measuring cavity which may have an axial axis, a cavity wall which may at least partly surround the measuring cavity which cavity wall is provided with a plurality of pinholes, the apparatus further comprising detection means which viewed from the measuring cavity, are provided behind the pin holes, wherein the detection means are arranged for in a position-dependent manner the detection of radioactive radiation emitted within the measuring cavity wherein the detection means can be read electronically or optically, wherein the apparatus is further provided with radiation blocking means which partly block radiation which travels from the measuring cavity through at least one of the pinholes to the detection means such that the radiation which is detected by the detection means lays in a limited solid angle relative to the at least one pinhole, which angle is smaller than the solid angle which would have been obtained without the radiation blocking means, wherein the radiation blocking means comprise a blocking wall extending between the cavity wall and the detection means wherein said blocking wall comprises a plurality of openings for providing a passage for the radiation from the pinholes to the detection means laying within said limited solid angle, and wherein the openings of the blocking wall have a surface which is greater than the surface of the pinholes.

46. An apparatus according to claim 45, wherein the detection means comprise a detector arrays wherein the radiation blocking means are arranged such that each detector array only receives radiation coming from one of the pinholes.

47. An apparatus according to claim 46, wherein the radiation blocking means comprises baffles.

48. An apparatus according to claim 47, wherein the baffles are located outside the measuring cavity.

49. An apparatus according to claim 45, wherein the baffles are arranged between the cavity wall and the detection means.

50. An apparatus according to claim 49, wherein the baffles are adjacent the cavity wall.

51. An apparatus according to claim 49, wherein the baffles are adjacent the detection means.

52. An apparatus according to claim 51, wherein the baffles each lay substantially in a plane through said axial axis.

53. An apparatus according to claim 52, wherein the baffles are provided with projecting elements having a direction component parallel to the surface of the detection means.

54. An apparatus according to claim 45, wherein each opening of the blocking wall corresponds with one of the pinholes such that the radiation which passes through one of the openings comes from a single one of the pinholes.

55. An apparatus according to claim 54, wherein the blocking wall has a shape which is substantially similar to the shape of the wall of the measuring cavity.

56. An apparatus according to claim 55 wherein the blocking wall comprises at least substantially flat wall segments having the openings wherein an edge directed in the axial direction of at least one of the wall segments is adjacent to a selectable portion of a neighboring wall segment said portion being directed in the direction of the axial axis and being directed to the measuring cavity so that the diameter of a space which is at least partly surrounded by the blocking wall and which space comprises the measuring cavity can be varied by selecting the distance between said portion of said neighboring wall segment and an edge directed in the direction of the axial axis of said neighboring wall segment.

57. An apparatus according to claim 56, wherein the blocking wall is of a rotationally symmetrical design around the axial axis of the measuring cavity.

58. An apparatus according to claim 57, wherein the blocking wall has a polygonal cross section in a direction perpendicular to the axial axis.

59. An apparatus according to claim 58, wherein polygonal cross section comprises n angles (n greater than or equal to 3).

60. An apparatus according to claim 59, wherein the blocking wall comprises n wall segments and/or that the detection means comprises n detectors.

61. An apparatus according to claim 60, wherein the measuring cavity has a polygonal cross section in a direction perpendicular to the axial axis and the cavity wall comprises at least substantially flat wall segments having the pinholes.

62. An apparatus according to claim 61, wherein pinholes that are located nearer the ribs of the polygonal measuring cavity are at an angle to the normal of the wall segment in the direction of the axial axis.

63. An apparatus according to claim 62, wherein neighboring pinholes laying substantial in a plane perpendicular to the axial axis and being near one of the nbs of the polygonal measuring cavity are spaced further apart than neighboring pinholes laying substantial in the plane perpendicular to the axial axis and laying substantial in the middle between two adjacent ribs.

64. An apparatus according to claim 63 wherein pinholes situated relatively close to the axial ends of the measuring cavity are at an angle to the normal of the wall segment in the direction of the absolute centre of the measuring cavity.

65. An apparatus according to claim 64, wherein the pinholes are distributed over the wall of the measuring cavity such that for two peripherally neighboring pinholes (pinholes separated in a direction perpendicular to the axial axis) one axially neighboring pinhole is situated halfway 50±20% between the two peripheral neighoring pinholes.

66. An apparatus according to claim 65, wherein the pinhole is rectangular.

67. An apparatus according to claim 66, wherein a detection means placed behind a pinhole is a detector array.

68. An apparatus according to claim 67, wherein a detection means Di situated behind a pinhole Pi comprises at least two detection means segments placed at an angle in relation to one another and out of plane, such that radiation from pinhole Pi reaching the detection means segment will on average have a more perpendicular line of incidence than if they were placed in a plane wherein i=1, 2, 3, . . . n wherein n is the total number of pinholes.

69. An apparatus according to claim 68, wherein a detection means Di situated behind a pinhole Pi has a curved surface, such that the radiation from pinhole Pi will on average have a more perpendicular line of incidence onto each part of the detection means Di wherein i=1, 2, 3, . . . n wherein n is the total number of pinholes.

70. An apparatus according to claim 60, wherein the blocking wall may be arranged to be replaceable by another blocking wall comprising other dimensions and/or other patterns of openings and/or openings with other dimensions.

71. An apparatus for obtaining a tomographic image of a human being or part of a human being or an animal or a part thereof using radioactive radiation, which apparatus comprises a measuring cavity provided with a plurality of pinholes, the measuring cavity being arranged to at least partly surround the animal where, viewed from the measuring cavity detection means D are provided behind the pin holes, where the detection means D are suitable for in a position-dependent manner detecting radioactive radiation and that the detection means D can be read electronically or optically, wherein the wall of the measuring cavity possesses an array of pinholes, wherein the axial component of the distance between two in axial direction neighboring pinholes is smaller than the transversal component of the distance between two neighboring pinholes located in transversal direction with respect to the axial direction, in that a pinhole $P_1$ has a maximum angle of incidence $\alpha i$ with respect to the normal and a detection means Di located behind that pinhole, and in that means comprising baffles are provided to limit the chance that via pinhole Pi radiation reaches any detection means D other than detection means Di,
- wherein the baffles are oriented towards the lumen of the measuring cavity,
- wherein the baffles are mounted on, around, or up against the surface of the detection means,
- wherein the baffles are provided with projecting elements having a direction component parallel to the surface of the detection means,
- and wherein the pinholes are distributed over the wall of the measuring cavity such that for two peripherally neighboring pinholes one axially neighboring pinhole is situated halfway ±20% between the two peripheral neighboring pinholes.

72. An apparatus according to claim 71, wherein the pinhole is rectangular.

73. An apparatus claim 72, wherein a detection means placed behind a pinhole is a detector array.

74. An apparatus according to claim 73, wherein the measuring cavity has a polygonal cross section and the wall is divided into wall segments having pinholes.

75. An apparatus according to claim 74, wherein pinholes that are located nearer the ribs of the polygonal measuring cavity are at an angle to the normal of the wall segment in the direction of the centre line of the polygonal measuring cavity.

76. An apparatus according to claim 74, wherein pinholes near one of the ribs of the polygonal measuring cavity are spaced further apart than pinholes nearer to the middle between two adjacent ribs.

77. An apparatus according to claim 76, wherein pinholes situated nearer the axial ends of the measuring cavity are at an angle to the normal of the wall segment in the direction of the absolute centre of the measuring cavity.

78. An apparatus according to claim 77, wherein at least 3 transversally spaced from one another and axially nearest neighboring pinholes Pi are axially staggered in relation to one another.

79. An apparatus according to claim 78, wherein a detection means Di situated behind a pinhole Pi comprises at least two detection means segments placed at an angle in relation to one another and out of plane, such that radiation from pinhole Pi reaching the detection means segment will on average have a more perpendicular line of incidence than if they were placed in a plane.

80. An apparatus according to claim 79, wherein a detection means Di situated behind a pinhole Pi has a curved surface, such that the radiation from pinhole Pi will on average have a more perpendicular line of incidence onto each part of the detection means Di.

81. An apparatus according to claim 80, wherein the cavity wall may be arranged to be replaceable by another cavity wall comprising other dimensions and/or other patterns of pinholes and/or pinholes with other dimensions.

82. An apparatus according to claim 74, wherein at least one of the baffles is retractable so that, in use, the retracted baffle will not be illuminated by the radiation from the cavity.

83. An apparatus for obtaining a tomographic image of a human being or part of a human being or an animal or a part thereof using radioactive radiation, which apparatus comprises a measuring cavity which may have an axial axis, a cavity wall which may at least partly surround the measuring cavity which cavity wall is provided with a plurality of pinholes, the apparatus further comprising detection means which viewed from the measuring cavity, are provided behind the pin holes, wherein the detection means are arranged for in a position-dependent manner the detection of radioactive radiation emitted within the measuring cavity wherein the detection means can be read electronically or optically, wherein the apparatus is further provided with radiation blocking means which partly block radiation which travels from the measuring cavity through at least one of the pinholes to the detection means such that the radiation which is detected by the detection means lays in a limited solid angle relative to the at least one pinhole, which angle is smaller than the solid angle which would have been obtained without the radiation blocking means, wherein the radiation blocking means comprises baffles and wherein the baffles are located outside the measuring cavity.

84. An apparatus according to claim 83 wherein the baffles are located inside the measuring cavity.

85. An apparatus according to claim 84, wherein the baffles are located adjacent the cavity wall.

86. An apparatus for obtaining a tomographic image of a human being or part of a human being or an animal or a part thereof using radioactive radiation, which apparatus comprises a measuring cavity having an axial axis, a cavity wall which at least partly surrounds the measuring cavity which cavity wall is provided with a plurality of pinholes, the apparatus further comprising detection means which viewed from the cavity, are provided behind the pin holes, wherein the detection means are arranged for receiving, in a position-related manner, the radioactive radiation emitted within the measuring cavity and wherein the detection means can be read electronically or optically, wherein:
- the pinholes are at least substantially arranged in a plurality of flat planes which planes are at least substantial parallel and separated in the direction of the axial axis relative to each other wherein the distance between neighboring planes is smaller than the distance between neighboring pinholes within any of such planes, and wherein the distance between neighboring planes is 0.03–0.98 and more preferably 0.05–0.77 times the distance between neighboring pinholes within any of such planes.

87. A method of obtaining a tomographic image of part of an animal or a part of an animal including a human being or a part of a human being by using radioactive radiation, wherein the animal is at least partly placed into a measuring cavity having an axial axis, the measuring cavity being at least partially surrounded by a cavity wall which is provided with a plurality of pinholes, and wherein behind the pin holes (as viewed from the measuring cavity or lumen) detection means are placed, radioactive radiation from a radioactive isotope administered to the animal is detected in a position-related manner by the detection means and data obtained with the detection means are used for the generation of the tomographic image, wherein:

the pinholes are at least substantially arranged in a plurality of flat planes which planes are at least substantially parallel and separated in the direction of the axial axis relative to each other wherein the distance between neighboring planes is smaller than the distance between neighboring pinholes within such a plane and, wherein the distance between neighboring planes is 0.03–0.98 and more preferably 0.05–0.77 times the distance between neighboring pinholes within any of such planes.

88. A method of obtaining a tomographic image of part of an animal or a part of an animal including a human being or a part of a human being by using radioactive radiation, wherein the animal is at least partly placed into a measuring cavity having an axial axis, the measuring cavity being at least partially surrounded by a cavity wall which is provided with a plurality of pinholes, and wherein behind the pin holes (as viewed from the measuring cavity) detection means are placed, radioactive radiation from a radioactive isotope administered to the animal is detected in a position-related manner by the detection means and data obtained with the detection means are used for the generation of the tomographic image, wherein:

the pinholes are at least substantially arranged along a helix wherein the pitch of the helix is generally smaller than the distance between neighboring pinholes laying on the helix; and wherein the pitch of the helix is 0.03–0.98and more preferably 0.05–0.77 times the distance between neighboring pinholes laying on the helix.

89. A method of obtaining a tomographic image of part of an animal or a part of an animal including a human being or a part of a human being by using radioactive radiation, wherein the animal is at least partly placed into a measuring cavity having an axial axis, the measuring cavity being at least partially surrounded by a cavity wall which is provided with a plurality of pinholes, and wherein behind the pin holes (as viewed from the measuring cavity or) detection means are placed, radioactive radiation from a radioactive isotope administered to the animal is detected in a position-related manner by the detection means and data obtained with the detection means are used for the generation of the tomographic image, wherein:

the pinholes are substantially arranged along a helix wherein the pitch of the helix is generally smaller than the distance between neighboring pinholes laying on the helix wherein the pitch of the helix is generally at least 1.03, at least 1.05, at least 1.3, more specifically at least 2, preferably at least 5 or more preferably at least 10 times smaller than the distance between neighboring pinholes laying along the helix.

* * * * *